United States Patent [19]

Yaegashi et al.

[11] Patent Number: 5,843,954

[45] Date of Patent: Dec. 1, 1998

[54] CAMPTOTHECIN DERIVATIVES, PREPARATIONS THEREOF AND ANTITUMOR AGENTS

[75] Inventors: Takashi Yaegashi, Kanagawa-ken; Seigo Sawada, Tokyo; Tomio Furuta, Tokyo; Teruo Yokokura, Tokyo, all of Japan

[73] Assignees: Kabushiki Kaisha Yakult Honsha; Daiichi Pharmaceutical Co., Ltd., both of Tokyo, Japan

[21] Appl. No.: 976,398

[22] Filed: Nov. 21, 1997

Related U.S. Application Data

[63] Continuation of Ser. No. 522,785, Sep. 1, 1995.

[30] Foreign Application Priority Data

Sep. 6, 1994 [JP] Japan .................................. 6-246660

[51] Int. Cl.⁶ .................................................. C07D 487/02
[52] U.S. Cl. ............................................. 514/285; 546/70
[58] Field of Search ................................ 514/285; 546/70

[56] References Cited

U.S. PATENT DOCUMENTS

| 4,914,205 | 4/1990 | Sawada et al. .......................... 546/70 |
| 5,122,606 | 6/1992 | Wani et al. . | |

FOREIGN PATENT DOCUMENTS

| 0 296 612 | 6/1988 | European Pat. Off. . |
| A S58-39684 | 3/1983 | Japan . |
| A 258-134095 | 8/1983 | Japan . |
| A S59-51287 | 3/1984 | Japan . |
| A S59-51289 | 3/1989 | Japan . |
| A H1-131179 | 5/1989 | Japan . |
| A H1-186892 | 7/1989 | Japan . |
| A H1-279891 | 11/1989 | Japan . |
| A H4-503505 | 6/1992 | Japan . |
| A H5-502017 | 4/1993 | Japan . |
| WO90/03169 | 4/1990 | WIPO . |
| WO91/04260 | 4/1991 | WIPO . |
| WO92/11263 | 7/1992 | WIPO . |

OTHER PUBLICATIONS

Yaegashi, et al Chem Pharm Bull vol. 42, No. 12 pp. 2518–2825 (Dec. 1994).

Seigo Sawada et al., "Chemical Modification of an Antitumor Alkloid, 20(S)–Camptothecin: E–Lactone Ring–Modified Water–Soluble Derivatives of 7–Ethylcamptothecin", Chem. Pharm. Bull. 41(2):310–313, 1993.

Primary Examiner—Donald G. Daus
Attorney, Agent, or Firm—Darby & Darby

[57] ABSTRACT

New camptothecin derivatives of the general formula (1):

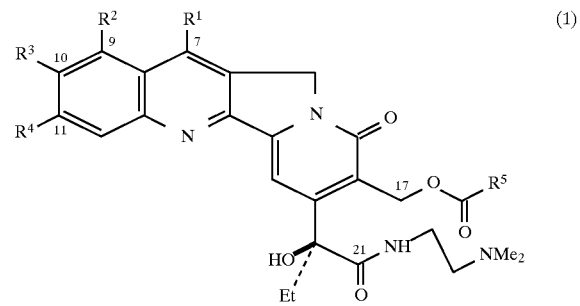

wherein $R^1$ represents a hydrogen atom or a $C_1$–$C_6$ alkyl group, $R^2$ represents a hydrogen or a $C_1$–$C_6$ alkoxy group, $R^3$ represents a hydrogen or halogen atom or a $C_1$–$C_6$ alkyl, $C_1$–$C_6$ alkoxy, hydroxyl, $C_2$–$C_6$ acyloxy or methoxyethoxymethoxy group, $R^4$ represents a hydrogen or halogen atom, and $R^5$ represents a $C_1$–$C_6$ alkyl, $C_3$–$C_6$ unsaturated alkyl, alkylthioalkyl, alkoxyalkyl, pyridyl or substituted phenyl group, with the proviso that all of the $R^2$, $R^3$ and $R^4$ substituents should not be a hydrogen atom, and a process for preparing the new camptothecin derivatives by subjecting the camptothecin derivatives of the general formula (2):

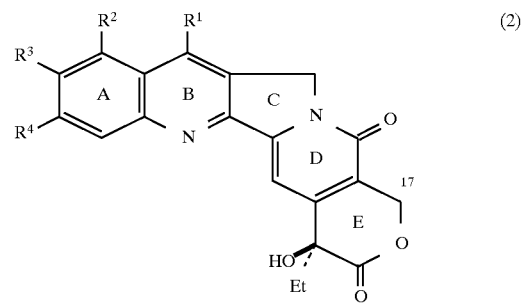

wherein $R^1$, $R^2$, $R^3$ and $R^4$ have the same meanings as given above, to the reaction with N,N-dimethylethylenediamine without solvent to open the E-lactone ring followed by acylation of 17-hydroxyl group with corresponding acylating agents and an antitumor agent containing the same as an active ingredient.

2 Claims, No Drawings

CAMPTOTHECIN DERIVATIVES, PREPARATIONS THEREOF AND ANTITUMOR AGENTS

This is a continuation of application Ser. No. 08/522,785, filed Sep. 1, 1995.

BACKGROUND OF THE INVENTION

1. Field of the Invention

The present invention relates to new water-soluble camptothecin derivatives, a process of the preparation thereof and antitumor agents containing the same as an active ingredient.

2. Description of the Prior Art

The present inventors have made an exploratory research and provided a number of new camptothecin (hereinafter referred to CPT) derivatives with excellent antitumor activities, and found that totally synthetic CPT derivatives carrying a lower alkyl group in 7-position on the B-ring and also hetero substituent and/or alkyl group in 9-, 10- and 11-position on the A-ring among others showed strong antitumor activity (see JP, A, H1-186892).

The present inventors have also made extensive researches to make the derivatives water-soluble by various means in order to solve a problem in case of administration. Especially, CPT derivatives synthesized by subjecting 7-ethylCPT to open the E-lactone ring by the diamines followed by acylation of the hydroxymethyl group showed excellent water solubility without decrease of antitumor activity contrasting to the known E-ring opened water soluble CPT derivatives (see JP, A, H1-131179 or U.S. Pat. No. 4,914,205).

In addtion to further research to obtain other new CPT derivatives with more excellent antitumor activity and with useful water solubility in case of administration, there is also a great demand in the art for creating new CPT derivatives which solve both toxicity and usage problems.

BRIEF SUMMARY OF THE INVENTION

Accordingly, an object of this invention is to provide new CPT derivatives possessing excellent characteristics in an antitumor activity. It is another object to provide new CPT derivatives which solve water solubility problem. In order to achieve those objects, we provided a process for the preparation of new water-soluble CPT derivatives prepared from CPT derivatives carrying a lower alkyl group in 7-position on the B-ring and also hetero substituent and/or alkyl group in 9-, 10- and 11-position on the A-ring by subjecting them to open the E-lactone ring by the diamines followed by acylation of the hydroxymethyl group. As a result of our extensive safety and galenical researches made for these new water-soluble CPT derivatives, it has been realized to achieve the above mentioned objects, and we succeeded in providing excellent new CPT derivatives as an antitumor agent in the invention.

DETAILED DESCRIPTION OF THE INVENTION

In accordance with the present invention, there are provided new CPT derivatives represented by the general formula:

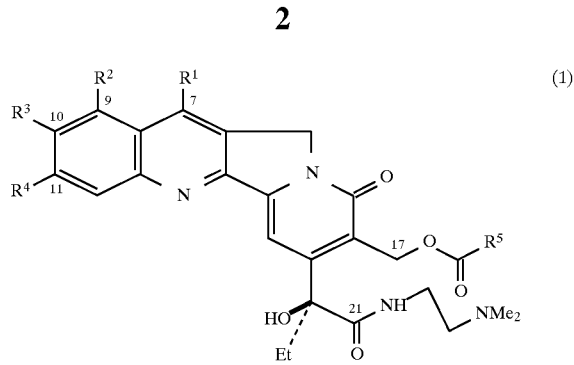

wherein $R^1$ represents a hydrogen atom or a $C_1$–$C_6$ alkyl group, $R^2$ represents a hydrogen or a $C_1$–$C_6$ alkoxy group, $R^3$ represents a hydrogen or halogen atom or a $C_1$–$C_6$ alkyl, $C_1$–$C_6$ alkoxy, hydroxyl, $C_2$–$C_6$ acyloxy or methoxyethoxymethoxy group, $R^4$ represents a hydrogen or halogen atom, and $R^5$ represents a $C_1$–$C_6$ alkyl, $C_3$–$C_6$ unsaturated alkyl, alkylthioalkyl, alkoxyalkyl, pyridyl or substituted phenyl group, with the proviso that all of the $R^2$, $R^3$ and $R^4$ substituents should not be a hydrogen atom, and a process for preparing new camptothecin derivatives. In further accordance with the present invention, there are provided antitumor agents containing new CPT derivatives of general formula (1) as an active ingredient.

The new CPT derivatives of the invention are prepared from CPT derivatives carrying a hydrogen atom or a lower alkyl group in 7-position and also hetero and/or alkyl group in 9-, 10- and 11-position by N,N-dimethylethylenediamine without solvent followed by acylation of 17-hydroxymethyl group with appropriate acylating agents. The starting CPT derivatives carrying a hydrogen atom or a lower alkyl group in 7-position and also hetero substituent and/or alkyl group in 9-, 10- and 11-position are the known CPT derivatives (9-methoxyCPT, 10-hydroxyCPT, 10-methoxyCPT, 11-hydroxyCPT, 11-methoxyCPT etc.) prepared from natural substances or are obtained semisynthetically or synthetically by the known procedures (see JP, A, S58-39684 U.S. Pat. Nos. 4,473,692 and 4,545,880; JP, A, S58-134095 or U.S. Pat. Nos. 4,473,692 and 4,545,880; JP, A, S59-51287 or U.S. Pat. No. 4,604,463; JP, A, S59-51289 or U.S. Pat. No. 4,604,463; JP, A, H1-279891 or U.S. Pat. Nos. 4,939,255 and 5,061,795; JP, A, H1-186892 U.S. Pat. No. 5,061,800; JP, A, H4-503505; JP, A, H5-502017; WO-91/04260; WO-92/11263; U.S. Pat. No. , 5,122,606 and others).

Although a reaction condition disclosed by in JP, A, H1-131179 U.S. Pat. No. 4,914,205 by us for the E-ring opening by N,N-dimethylethylenediamine followed by acylation of 17-hydroxyl group with appropriate acylating agents can be applied, it has been found that aimed compounds were not necessarily prepared in satisfactory yields according to this procedure. We have examined reaction conditions of this procedure and found that in the first step of the E-lactone ring opening reaction by N,N-dimethylethylenediamine, using an excess amount of N,N-dimethylethylenediamine alone without solvent gave the E-ring opened intermediate followed by acylation of 17-hydroxyl group with appropriate acylating agents to afford the aimed compounds in very good yields.

As the acylating agent used for the acylation there is no specific agent, but corresponding acid anhydrides, acid halogenides, for example, acid chlorides, acid bromides and other equivalent acylating agents can be used. A reaction mixture of a corresponding carboxylic acid treated with a condensation agent, for example, dicyclohexylcarbodiimide can be also used for the said acylation.

Illustrative of the corresponding carboxylic acids used as the said acylating agents are, for example, saturated aliphatic acids with 2–20 carbon atoms, unsaturated aliphatic acids with 3–20 carbon atoms, aliphatic acids with a cycloalkyl group, or aliphatic acids with, for example, a halogen atom or alkylthio, amino, acylamino, hydroxyl, alkoxy, or alkoxycarbonyl group, aromatic acids with 6–20 carbon atoms or aromatic acids with, for example, a halogen atom or hydroxyl, alkoxy or lower alkyl group, heteroaromatic acids or amino acids. Examples of the acylating agents include acetyl chloride, benzoyl chloride, propionyl chloride, butyryl chloride, methoxybenzoyl chloride, fluorobenzoyl chloride, bromobenzoyl chloride, chlorobenzoyl chloride, nitrobenzoyl chloride, trifluoromethylbenzoyl chloride, naphthoyl chloride, cyclopropanecarbonyl chloride, thenoyl chloride, crotonyl chloride, cinnamoyl chloride, phenylacetyl chloride, phenylbenzoyl chloride, cyclohexanecarbonyl chloride, stearoyl chloride, oleoyl chloride, methoxycarbonylbezoyl chloride, ethyl succinyl chloride, linoleyl chloride, chlorobutyryl chloride, ethylbenzoyl chloride, methylthiopropionyl chloride, pivaloyl chloride, nicotinoyl chloride, isonicotinoyl chloride and picolinoyl chloride.

In the said acylation N,N-dimethylaminopyridine or the like can be present in the reaction as a catalyst.

In adding, to keep carefully an anhydrous condition not only in the ring-opening process but in the acylation process and further, for example, in the pulverization, the purification and the crystallization process can increase a yield of an aimed compound.

The new CPT derivatives of this invention show excellent water solubility by being converted to acid addition salts thereof with proper acids such as hydrochloric acid. The compounds of this invention show excellent results in safety and in antitumor activity and therefore can be provided as new antitumor agents.

The present invention will now be illustrated in more detail by way of examples.

SYNTHETIC EXAMPLES

General Synthetic Methods

Example 1
Preparation of ring-opened compounds ($B_1$–$B_{13}$)

As a starting material CPT derivatives ($A_1$–$A_{12}$, for each substituent refer Table 1) with each substituent in 7-position and in 9-, 10- and 11-position on the A-ring were prepared according to the above mentioned literature. 9-Methoxy CPT($A_{13}$) isolated from natural substances was employed in this example. And for the compounds carrying hydroxyl group on the A-ring, the compound ($A_{10}'$) which was obtained by a usual O-methoxyethoxymethylation was used.

To 3.0 g, for example, of the starting CPT derivative ($A_1$–$A_{13}$) was added excess anhydrous N,N-dimethylethylenediamine (5–100 eq. for example 15 ml). The reaction mixture was stirred under nitrogen at 50° C. for 1.5 hr. After reacted the reaction mixture was evaporated to dryness under reduced pressure. The residue was dissolved in dry methylene chloride (for example 15 ml), and the solution was poured into large amount of dry n-hexane (for example 500 ml). The precipitated crystals were filtered, washed with dry n-hexane and dried to give the hydroxyamide ($B_1$–$B_{13}$, E-lactone-ring opened compounds) in an almost quantitative yield.

The yields and each spectral data are shown in the following Table 2.

Example 2
Acylation of the 17-hydroxyl group

To a solution of the above obtained hydroxyamide (for example 1.0 g) in dry methylene chloride (for example 20 ml) was added dropwise an acylating agent (1.2 eq.)in presence of dimethylaminopyridine (DMPA, for example 100 mg) under ice cooling. The reaction mixture was stirred at room temperature overnight and washed with 7% aqueous sodium hydrogen bicarbonate and saturated aqueous sodium chloride solution. The methylene chloride layer was dried over anhydrous sodium sulfate, followed by removal of insoluble materials, and evaporated to dryness under reduced pressure. The residue was subjected to silica gel column chromatography (10% MeOH—$CHCl_3$) and crystallized from chloroform-n-hexane to give the 17-O-acyl-21-N, N-dimethylaminoethylamide derivative ($C_1$–$C_{48}$) related to the invention.

As for an O-methoxyethoxymethyl derivative a solution of the compound in 10% trifluoroacetic acid-methylene chloride was stirred overnight. After stirring triethylamine (eq. mol) was added dropwise under ice cooling to the reaction mixture. The reaction mixture was evaporated to dryness under reduced pressure. The residue was dissolved in methylene chloride, washed with 7% aqueous sodium hydrogen bicarbonate and saturated aqueous sodium chloride solution. The organic layer was dried over anhydrous sodium sulfate, followed by removal of insoluble materials, and evaporated to dryness under reduced pressure. The residue was subjected to silica gel column chromatography (10% MeOH—$CHCl_3$) and crystallized from acetone-$CHCl_3$ to give the 17-O-acyl-21-N,N-dimethylaminoethylamide derivative ($C_{28}$, $C_{30}$, $C_{32}$, $C_{34}$, $C_{36}$, $C_{38}$) related to the invention.

The yields of the synthesized derivatives and their spectral data are shown in Table 1 and Table 3.

The water solubility data of the obtained new camptothecin derivatives related to the invention are shown in Table 4.

[Antitumor Effect]

For the obtained new camptothecin derivatives of the invention, their results of antitumor activity, toxicology test, usage-dose, and galenical preparation are described below.

[Antitumor Activity]

It is well accepted that antitumor effect for a rodent leads to a reliable result for antitumor effect in a warm-blooded animal. The present inventors investigated antitumor effect for mice as a model.

[Antitumor activity for $L_{1210}$]

$5 \times 10^5$ cells of mouse leukemia $L_{1210}$ were transplanted intraperitoneally to a group of six female $CDF_1$ mice (7 weeks old, body weight 17–19 g). The test compound was administered intraperitoneally on day 1, 5 and 9 and its life prolonging effect was observed.

In a case of the administration of a test compound as an acid addition salt the test compound was dissolved in water. The total administration amount was 1.56 mg/kg–400 mg/kg. The antitumor activity was expressed by the value (T/C%) wherein T denotes the mean survival days in the drug administered group and C denotes those in the non administered group. In case of equal to or more than 125% the drug is considered to be effective. A therapeutic index was calculated by examining the least effective dose and the maximum tolerance dose.

[Experimental Result]

The antitumor experimental results of the compounds described in the previous example are shown in Table 5. As shown in Table 5, the new camptothecin derivatives in the present invention showed about 6 fold more favorable therapeutic index than camptothecin itself. At an optimum dose there was the case that 5 mice among 6 mice in the group survived. The results also show their effectiveness at lower doses, remarkable increase of antitumor activity and enlargement of a therapeutic margin.

[Toxicity Experiment]

Acute toxicity test was conducted by intraperitoneal administration using a group of twenty ICR male mice (4 weeks old, body weight around 20 g). The results are shown in Table 6.

$LD_{50}$ value was calculated by the Richfield-Willcokson method from a lethal ratio observing the fate of mice during 1 week after administration of a test compound.

From the above experimental results, it is understood that the new camptothecin derivatives have better antitumor activity and can be used as less toxic drugs than their mother compound, camptothecin, for a treatment of cancer.

The antitumor agents of the present invention can be administered by a injection such as intravenous, intradermal and intramuscular injection, and by oral administration. Especially preferable examples are to administer the compounds as their acid-addition salts appropriate as medicaments by intravenous or oral administration.

In an intravenous administration, the dose of each compound above mentioned depends upon the aim of a therapeutic treatment, and is in range 5–400 mg/body per day, preferably 20–200 mg/body for adults. In an oral administration a range 50–2000 mg/body per day, preferably 100–1000 mg/body for adults.

As a preparation method of the antitumor agents of the present invention, a usual method for each preparation can be selected according to a formulation. As a formulation suitable for absorption through stomach intestine, the antitumor agents of the invention may be prepared in, for example, tablet, powder, granule, capsule or soft capsule, and examples of the oral liquid preparation include water or oil suspension, solution, syrup and elixir etc. A preparation for injection may be stored in an ample or a large container. In these formulation an excipient such an antiseptic or dissolvent can be used.

A formulation of a liquid preparation may be suspension, solution and emulsion with oily or aqueous vehicle, and may include an excipient such as emulsifier. Corresponding to a preparation of the antitumor agents of the invention, a content of the active drug is 0.1% or more, preferably 1–50%.

The preparation examples of the antitumor agents of the invention are further illustrated in, though not limited by, the following examples.

Preparation 1 Injection

After dissolving the compound $C_7$ ($R^1=C_2H_5$, $R^2=H$, $R^3=CH_3$, $R^4=H$, $R^5=C_2H_4SCH_3$) in 0.1N HCl containing equivalent molar HCl , the solution was filtered, and lyophilized to give 50 mg of the HCl salt of the compound C7. The salt was sealed into an ample in a germfree condition and stored under cooling in the dark.

Preparation 2 Tablet

| | |
|---|---|
| Compound $C_7$ | 50 mg |
| Lactose | 89 mg |
| Hydroxypropylcellulose | 2.7 mg |
| Crystalline cellulose | 15 mg |
| Talc | 1.6 mg |
| Magnesium stearate | 1.7 mg |

The above ingredients were mixed and formed directly into tablets (160 mg/tablet) using a tablet machine.

TABLE 1

(Yields of each compounds)

$A_{1\_13}$ $\longrightarrow$ $B_{1\_13}$ $\longrightarrow$

Starting Compd.   Hydroxy Amide Compd.

$C_{1\_48}$ $\longrightarrow$ $C_{28, 30, 32, 34, 36, 38}$ 17-0-Acyl Compd.   Deprotection

| | | | | | | | Yield (%) | |
|---|---|---|---|---|---|---|---|---|
| Compd. No. | A | $R^1$ | $R^2$ | $R^3$ | $R^4$ | $R^5$ | A→B | B→C |
| $C_1$ | $A_{11}$ | Me | H | OEt | H | $-CH_2CH_2SMe$ | 98 | 38 |
| $C_2$ | $A_{12}$ | " | " | H | Br | " | 99 | 26 |
| $C_3$ | $A_1$ | Et | " | Cl | H | Et | 94 | 51 |
| $C_4$ | $A_1$ | " | " | " | " | Pr | " | 50 |
| $C_5$ | $A_1$ | " | " | " | " | $-CH_2CH_2SMe$ | " | 47 |
| $C_6$ | $A_2$ | " | " | Br | " | " | 98 | 47 |
| $C_7$ | $A_3$ | " | " | Me | " | " | 98 | 43 |
| $C_8$ | $A_4$ | " | " | H | F | Et | 95 | 71 |
| $C_9$ | $A_4$ | " | " | " | F | Pr | " | 75 |
| $C_{10}$ | $A_4$ | " | " | " | " | $-CH_2CH_2SMe$ | " | 72 |
| $C_{11}$ | $A_4$ | " | " | " | " | $-C_6H_4-OMe$ | " | 59 |
| $C_{12}$ | $A_5$ | " | " | " | Cl | $-CH_2CH_2SMe$ | 92 | 30 |
| $C_{13}$ | $A_6$ | " | " | F | F | Et | 98 | 56 |
| $C_{14}$ | $A_6$ | " | " | " | " | Pr | " | 58 |
| $C_{15}$ | $A_6$ | " | " | " | " | $-CH_2CH_2SMe$ | " | 42 |
| $C_{16}$ | $A_6$ | Et | H | F | F | $-C_6H_4-OMe$ | 98 | 37 |
| $C_{17}$ | $A_7$ | " | " | Cl | Cl | Et | 92 | 59 |
| $C_{18}$ | $A_7$ | " | " | " | " | Pr | " | 60 |
| $C_{19}$ | $A_7$ | " | " | " | " | $-CH_2CH_2SMe$ | " | 56 |
| $C_{20}$ | $A_8$ | " | " | OMe | F | Et | 97 | 70 |
| $C_{21}$ | $A_8$ | " | " | " | " | Pr | " | 67 |
| $C_{22}$ | $A_8$ | " | " | " | " | $-CH_2CH_2SMe$ | " | 65 |
| $C_{23}$ | $A_9$ | " | " | Me | " | Et | 94 | 84 |
| $C_{24}$ | $A_9$ | " | " | " | " | Pr | " | 82 |
| $C_{25}$ | $A_9$ | " | " | " | " | $-CH_2CH_2SMe$ | " | 80 |
| $C_{26}$ | $A_9$ | Et | H | Me | F | $-C_6H_4-OMe$ | 94 | 78 |

TABLE 1-continued (Yields of each compounds)

$$A_{1\_13} \longrightarrow B_{1\_13} \longrightarrow$$
Starting Compd.   Hydroxy Amide Compd.

$$C_{1\_48} \longrightarrow C_{28, 30, 32, 34, 36, 38}$$
17-O-Acyl Compd.   Deprotection

| Compd. No. | A | R¹ | R² | R³ | R⁴ | R⁵ | Yield (%) A→B | B→C |
|---|---|---|---|---|---|---|---|---|
| C₂₇ | A₁₀ | " | " | OMEM | H | Et | 96 | 65 |
| C₂₈ |  | " | " | OH | " | " |  | x61 |
| C₂₉ | A₁₀ | " | " | OMEM | " | Pr | " | 64 |
| C₃₀ |  | " | " | OH | " | " |  | x65 |
| C₃₁ | A₁₀ | " | " | OMEM | " | —CH₂CH₂SMe | " | 68 |
| C₃₂ |  | " | " | OH | " | " |  | x60 |
| C₃₃ | A₁₀ | " | " | OMEM | " | —CH=CHCH₃ | " | 34 |
| C₃₄ |  | " | " | OH | " | " |  | x61 |
| C₃₅ | A₁₀ | " | " | OMEM | " | —C₆H₄—F$_{(p)}$ | " | 68 |
| C₃₆ |  | " | " | OH | " | " |  | x57 |
| C₃₇ | A₁₀ | Et | H | OMEM | H | —C₆H₄—F$_{(m)}$ | 96 | 65 |
| C₃₈ |  | " | " | OH | " | " |  | x58 |
| C₃₉ | A₃ | " | " | Me | " | -4-pyridyl | 98 | 89 |
| C₄₀ | A₁ | " | " | Cl | " | " | 94 | 75 |
| C₄₁ | A₄ | " | " | H | F | " | 95 | 93 |
| C₄₂ | A₉ | " | " | Me | " | " | 94 | 85 |
| C₄₃ | A₈ | " | " | OMe | " | " | 97 | 95 |
| C₄₄ | A₁₃ | H | OMe | H | H | -2-pyridyl | 96 | 80.8 |
| C₄₅ | A₁₀ | Et | H | OH | H | Me | — | — |
| C₄₆ | A₁₀ | " | " | " | " | iso-Pr | — | — |
| C₄₇ | A₁₀ | " | " | " | " | —C₂H₄OEt | — | — |
| C₄₈ | A₁₀ | " | " | OAc | " | —C₆H₄—F$_{(p)}$ | 83 | — |

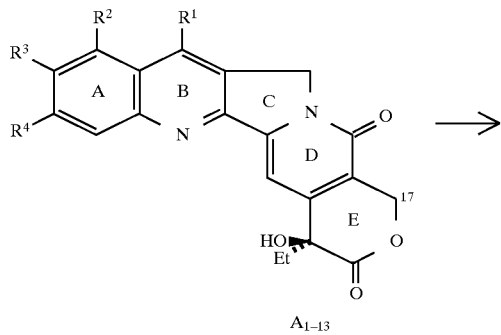

A₁₋₁₃

TABLE 1-continued

(Yields of each compounds)

A₁₋₁₃ → B₁₋₁₃ →
Starting Compd.   Hydroxy Amide Compd.

C₁₋₄₈ → C₂₈, 30, 32, 34, 36, 38
17-O-Acyl Compd.   Deprotection

| | | | | | | | Yield (%) | |
|---|---|---|---|---|---|---|---|---|
| Compd. No. | A | R¹ | R² | R³ | R⁴ | R⁵ | A→B | B→C |

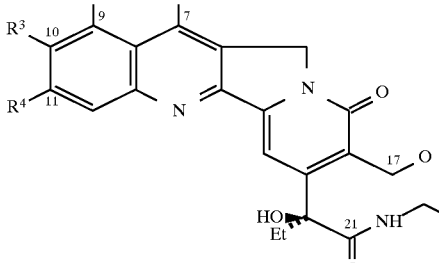

B₁₋₁₃

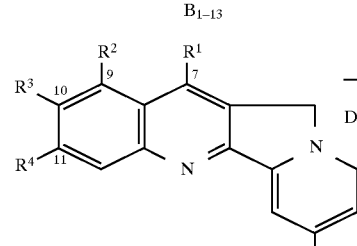

C₁₋₄₈

TABLE 2

(Spector Data of Hydroxy Amide Compounds)

B₁ (7-Et-10-Cl—)

Yellow powder (from n-Hexane-chloroform)
$C_{26}H_{31}N_4O_4Cl$, MS [M+H]⁺=499,
$IR_\nu^{MAX}/_{KBr}$ (cm⁻¹): 1650, 1590, 1510.
¹H-NMR(δppm) in CDCl₃: 1.10(3H, t, J=7Hz), 1.34(3H, t, J=8Hz), 2.20–2.32(1H, m), 2.27(6H, s), 2.39–2.61(3H, m), 2.90–3.05(2H, m), 3.20–3.33(1H, m), 3.60–3.75(1H, m), 4.78(1H, d, J=13Hz), 5.00(1H, d, J=19Hz), 5.06(1H, d, J=19Hz), 5.10(1H, d, J=13Hz), 7.44(1H, br-t, J=5Hz), 7.50(1H, s), 7.62(1H, dd, J=2, 9Hz), 7.82(1H, d, J=2Hz), 7.95(1H, d, J=9Hz).

B₂ (7-Et-10-Br—)

Pale yellow powder(from n-Hexane-chloroform)
$C_{26}H_{31}N_4O_4Br$, MS [M+H]⁺=543,
$IR_\nu^{MAX}/_{KBr}$(cm⁻¹): 1645, 1585, 1510.
¹H-NMR(δppm) in CDCl₃: 1.10(3H, t, J=7Hz), 1.35(3H, t, J=8Hz), 2.20–2.33(1H, m), 2.29(6H, s), 2.35–2.63(3H, m), 2.99(2H, q, J=8Hz), 3.20–3.35(1H, m), 3.60–3.75(1H, m), 4.78(1H, d, J=13Hz), 5.02(1H, d, J=19Hz), 5.07(1H, d, J=19Hz), 5.10(1H, d, J=13Hz), 7.43(1H, br-t, J=6Hz), 7.50(1H, s), 7.75(1H, dd, J=2, 9Hz), 7.88(1H, d, J=9Hz), 8.02(1H, d, J=2Hz).

B₃ (7-Et-10-Me—)

Colorless powder (from n-Hexane-chloroform)

TABLE 2-continued (Spector Data of Hydroxy Amide Compounds)

$C_{27}H_{34}N_4O_4$, MS [M+H]$^+$=479,
$IR_v{}^{MAX}/_{KBr}(cm^{-1})$: 1645, 1580, 1560, 1510.
$^1$H-NMR(δppm) in CDCl$_3$: 1.10(3H, t, J=7Hz), 1.32(3H, t, J=8Hz), 2.20–2.33(1H, m), 2.27(6H, s), 2.38–2.60(3H, m), 2.57(3H, s), 2.92–3.05(2H, m), 3.20–3.33(1H, m), 3.61–3.75(1H, m), 4.80(1H, d, J=14Hz), 5.02(1H, d, J=19Hz), 5.08 (1H, d, J=19Hz), 5.12(1H, d, J=14Hz), 7.34(1H, br-t, J=6Hz), 7.51(1H, s), 7.54 (1H, dd, J=2, 9Hz), 7.64(1H, br-s), 7.99(1H, d, J=9Hz).

B$_4$ (7-Et-11-F—)

Pale yellow powder(from n-Hexane-chloroform)
$C_{26}H_{31}N_4O_4F$, MS [M+H]$^+$=483,
$IR_v{}^{MAX}/_{KBr}(cm^{-1})$: 1645, 1590, 1510.
$^1$H-NMR(δppm) if CDCl$_3$: 1.10(3H, t, J=7Hz), 1.35(3H, t, J=8Hz), 2.20–2.33(1H, m), 2.28(6H, s), 2.38–2.62(3H, m), 2.97–3.14(2H, m), 3.20–3.33(1H, m), 3.63–3.76(1H, m), 4.78(1H, d, J=13Hz), 5.03(1H, d, J=19Hz), 5.08(1H, d, J=19Hz), 5.12(1H, d, J=13Hz), 7.32(1H, ddd, J=3, 8, 10Hz), 7.39(1H, br-t, J=6Hz), 7.51(1H, s), 7.67(1H, dd, J=3, 10Hz), 7.93(1H, dd, J=6, 9Hz).

B$_5$ (7-Et-11-Cl—)

Pale yellow powder(from n-Hexane-chloroform)
$C_{26}H_{31}N_4O_4Cl$, MS [M+H]$^+$=499,
$IR_v{}^{MAX}/_{KBr}(cm^{-1})$: 1645, 1600, 1590.
$^1$H-NMR(δppm) in CDCl$_3$: 1.10(3H, t, J=7hz), 1.36(3H, t, J=8Hz), 2.20–2.33(1H, m), 2.28(6H, s), 2.39–2.62(3H, m), 2.97–3.12(2H, m), 3.21–3.33(1H, m), 3.62–3.78(1H, m), 4.76(1H, d, J=14Hz), 5.00(1H, d, J=19Hz), 5.05(1H, d, J=19Hz), 5.10(1H, d, J=14Hz), 7.39–7.52(3H, m), 7.84(1H, d, J=9Hz), 7.97(1H, d, J=2Hz).

B$_6$ (7-Et-10, 11-F$_2$—)

Yellow powder (from n-Hexane-chloroform)
$C_{26}H_{30}N_4O_4F_2$, MS [M+H]$^+$=501,
$IR_v{}^{MAX}/_{KBr}(cm^{-1})$: 1645, 1590, 1515.
$^1$H-NMR(δppm) in CDCl$_3$: 1.10(3H, t, J=7hz), 1.36(3H, t, J=8Hz), 2.18–2.64(4H, m), 2.29(6H, s), 3.06(2H, q, J=8Hz), 3.22–3.37(1H, m), 3.60–3.78(1H, m), 4.76(1H, d, J=14Hz), 5.06(1H, d, J=19Hz), 5.11(1H, d, J=19Hz), 5.13(1H, d, J=14Hz), 7.36–7.44(1H, br), 7.51(1H, s), 7.69(1H, dd, J=8, 11Hz), 7.81(1H, dd, J=8, 11Hz).

B$_7$ (7-Et-10, 11-Cl$_2$—)

Yellow powder (from n-Hexane-chloroform)
$C_{26}H_{30}N_4O_4Cl_2$, MS [M+H]$^+$=533,
$IR_v{}^{MAX}/_{KBr}(cm^{-1})$: 1650, 1595, 1520.
$^1$H-NMR(δppm) in CDCl$_3$: 1.09(3H, t, J=7Hz), 1.38(3H, t, J=8Hz), 2.18–2.34(1H, m), 2.29(6H, s), 2.38–2.64(3H, m), 2.94–3.11(2H, m), 3.23–3.38(1H, m), 3.60–3.75(1H, m), 4.71(1H, d, J=14Hz), 4.97(1H, d, J=19Hz), 5.03(1H, d, J=19Hz), 5.06(1H, d, J=14Hz), 7.43(1H, s), 7.51(1H, br-t, J=5Hz), 7.94(1H, s), 8.02(1H, s).

B$_8$ (7-Et-10-OMe-11-F—)

Yellow powder(from n-Hexane-chloroform)
$C_{27}H_{33}N_4O_5F$, MS [M+H]$^+$=513,
$IR_v{}^{MAX}/_{KBr}(cm^{-1})$: 1650, 1590, 1510.
$^1$H-NMR(δppm) in CDCl$_3$: 1.11(3H, t, J=7Hz), 1.31(3H, t, J=8Hz), 2.20–2.37(1H, m), 2.27(6H, s), 2.41–2.60(3H, m), 2.85–3.04(2H, m), 3.21–3.33(1H, m), 3.60–3.73(1H, m), 4.00(3H, s), 4.73(1H, d, J=13Hz), 4.86(1H, d, J=19Hz), 4.94(1H, d, J=19Hz), 5.05(1H, d, J=13Hz), 6.93(1H, d, J=9Hz), 7.38(1H, s), 7.51(1H, br-t, J=6Hz), 7.55(1H, d, J=12Hz).

B$_9$ (7-Et-10-Me-11-F—)

Pale yellow powder(from n-Hexane-chloroform)
$C_{27}H_{33}N_4O_4F$, MS [M+H]$^+$=497,
$IR_v{}^{MAX}/_{KBr}(cm^{-1})$: 1645, 1585, 1505.
$^1$H-NMR(δppm) in CDCl$_3$: 1.10(3H, t, J=7hz), 1.35(3H, t, J=8Hz), 2.21–2.35(1H, m), 2.28(6H, s), 2.40–2.62(3H, m), 2.48(3H, s), 2.94–3.12(2H, m), 3.23–3.37(1H, m), 3.59–3.74(1H, m), 4.76(1H, d, J=13Hz), 4.95(1H, d, J=19Hz), 5.01(1H, d, J=19Hz), 5.09(1H, d, J=13Hz), 7.46(1H, s), 7.47(1H, br-t, J=6Hz), 7.52(1H, d, J=11Hz), 7.65(1H, d, J=8Hz).

B$_{10}$ (7-Et-10-OMEM—)

Yellow powder (from n-Hexane-chloroform)
$C_{30}H_{40}N_4O_7$, MS [M+H]$^+$=569,
$IR_v{}^{MAX}/_{KBr}(cm^{-1})$: 1650, 1625, 1585, 1510
$^1$H-NMR(δppm) in CDCl$_3$: 1.10(3H, t, J=7hz), 1.30(3H, t, J=8Hz), 2.20–2.33(1H, m), 2.26(6H, s), 2.39–2.61(3H, m), 2.87–3.03(2H, m), 3.24–3.33(1H, m), 3.39(3H, s), 3.52–3.73(3H, m), 3.83–3.94(2H, m), 4.80(1H, d, J=13Hz), 4.98(1H, d, J=19Hz), 5.04(1H, d, J=19Hz), 5.09(1H, d, J=13Hz), 5.40(1H, d, J=7hz), 5.43, (1H, d, J=7hz), 7.38–7.44(2H, m), 7.46(1H, s), 7.48(1H, br-t, J=6Hz), 7.97(1H, d, J=9Hz).

TABLE 2-continued (Spector Data of Hydroxy Amide Compounds)

$B_{11}$ (7-Me-10-OEt—)

Pale yellow powder(from n-Hexane-chloroform)
$C_{27}H_{34}N_4O_5$, MS $[M+H]^+$=495,
$IR_v^{MAX}/_{KBr}(cm^{-1})$: 1645, 1620, 1590, 1510.
$^1$H-NMR(δppm) in $CDCl_3$: 1.11(3H, t, J=7hz), 1.54(3H, t, J=7hz), 2.23–2.33(1H, m), 2.28(6H, s), 2.39(3H, s), 2.43–2.59(3H, m), 3.21–3.37(1H, m), 3.55–3.72(1H, m), 3.97–4.17(2H, m), 4.80(1H, d, J=13Hz), 4.81(1H, d, J=18Hz), 4.89(1H, d, J=18Hz), 5.01(1H, d, J=13Hz), 6.72(1H, d, J=3Hz), 7.30(1H, dd, J=3, 9Hz), 7.40(1H, s), 7.49(1H, br-t, J=6Hz), 7.90(1H, d, J=9Hz).

$B_{12}$ (7-Me-10-Br—)

Pale yellow powder(from n-Hexane-chloroform)
$C_{25}H_{29}N_4O_4Br$, MS $[M+H]^+$=529,
$IR_v^{MAX}/_{KBr}(cm^{-1})$: 1645, 1595, 1515.
$^1$H-NMR(δppm) in $CDCl_3$: 1.11(3H, t, J=7Hz), 2.18–2.33(1H, m), 2.29(6H, s), 2.40–2.65(3H, m), 2.60(3H, s), 3.20–3.35(1H, m), 3.60–3.75(1H, m), 4.77(1H, d, J=13Hz), 4.87(1H, d, J=19Hz), 4.93(1H, d, J=19Hz), 5.06(1H, d, J=13Hz), 7.40–7.48(2H, m), 7.51(1H, dd, J=2, 9Hz), 7.61(1H, d, J=9Hz), 8.14(1H, d, J=2Hz).

$B_{13}$ (9-OMe—)

Pale yellow powder(from n-Hexane-chloroform)
$C_{25}H_{30}N_4O_5$, MS $[M+H]^+$=467,
$IR_v^{MAX}/_{KBr}(cm^{-1})$: 3360, 1650, 1615, 1585, 1515.
$^1$H-NMR(δppm) in $CDCl_3$: 1.08(3H, t, J=7Hz), 2.18–2.34(1H, m), 2.23(6H, s), 2.38–2.57(3H, m), 3.16–3.29(1H, m), 3.58–3.72(1H, m), 3.96(3H, s), 4.79(1H, d, J=13Hz), 5.02(1H, d, J=19Hz), 5.08(1H, d, J=13Hz), 5.09(1H, d, J=19Hz), 6.77(1H, d, J=8Hz), 7.38(1H, br-t, J=5Hz), 7.50(1H, s), 7.57(1H, dd, J=8, 8Hz), 7.63(1H, d, J=8Hz), 8.50(1H, s).

TABLE 3

(Spectral Data of 17-O-Acyl-21-amide Compounds)

$C_1$ mp 101–106° C., Pale yellow needles (from n-Hexane-chloroform)
$C_{31}H_{40}N_4O_6S.H_2O$, MS $[M + H]^+$ = 597,
Anal., (C, H, N): Found (calcd.) 60.67, 6.58, 8.96 (60.57, 6.89, 9.11),
$IRv^{MAX}/_{KBr}$ (cm$^{-1}$): 1725, 1650, 1620, 1590, 1510
$^1$H-NM (δppm) in $CDCl_3$: 1.09(3H, t, J=7Hz), 1.54(3H, t, J=7Hz), 2.09(3H, s), 2.22–2.38(1H, m), 2.28(6H, s), 2.41–2.68(5H, m), 2.57(3H, s), 2.72–2.80(2H, m), 3.24–3.34(1H, m), 3.42–3.53(1H, m), 4.13(2H, q, J=7Hz), 4.82–5.37(1H, br), 4.96(1H, d, J=19Hz), 5.07(1H, d, J=19Hz), 5.49(1H, d, J=12Hz), 5.53(1H, d, J=12Hz), 6.88(1H, br-s), 7.35(1H, dd, J=3, 9Hz), 7.38(1H, br-t, J=6Hz), 7.49(1H; s), 7.98(1H, d, J=9Hz).

$C_2$ mp 108–118° C., Yellow powder (from n-Hexane-chloroform)
$C_{29}H_{35}N_4O_5BrS.½O$, MS $[M + H]^+$ = 631,
Anal. (C, H, N): Found (calcd.) 54.08, 5.76, 8.48 (54.37, 5.66, 8.75)
$IRv^{MAX}/_{KBr}$ (cm$^{-1}$): 1725, 1650, 1600, 1515.
$^1$H-NMR (δppm) in $CDCl_3$: 1.17 (3H, t, J=7Hz), 2.09(3H, s), 2.22–2.38(1H, m), 2.29(6H, s), 2.43–2.82(7H, m), 2.65(3H, s), 3.24–3.35(1H, m), 3.44–3.57(1H, m), 4.91(1H, d, J=19Hz), 5.01(1H, d, J=19Hz), 5.49(2H, s), 7.48(1H, dd, J=2, 9Hz; 1H, s), 7.53(1H, br-t, J=6Hz), 7.59(1H, d, J=9Hz), 8.14(1H, d, J=2Hz).

$C_3$ mp 130–133° C., Yellow powder (from n-Hexane-chloroform),
$[α]^{25}/_D$ = +27.5($CH_3OH$, c = 0.2), $C_{29}H_{35}N_4O_5Cl.½H_2O$, MS $[M + H]^+$ = 555,
Anal. (C, H, N): Found (calcd.) 61.74, 6.43, 9.66 (61.75, 6.43, 9.93),
$IRv^{MAX}/_{KBr}$ (cm$^{-1}$): 1730, 1650, 1600, 1515.
$^1$H-NHR (δppm) in $CDCl_3$: 1.11(3H, t, J=7Hz), 1.12(3H, t, J=7Hz), 1.34(3H, t, J=8Hz), 2.20–2.59(6H, m), 2.26(6H, s), 2.92–3.10(2H, m), 3.21–3.35(1H, m), 3.38–3.51(1H, m), 4.99(1H, d, J=19Hz), 5.10( 1H, d, J=19Hz), 5.26–5.60(1H, br), 5.47(1H, d, J=12Hz), 5.50(1H, d, J=12Hz), 7.43(1H, br-t, J=5Hz), 7.49(1H, s), 7.62(1H, dd, J=2, 9Hz), 7.73(1H, d, J=2Hz); 7.92(1H, d, J=9Hz).

$C_4$ mp 136–138° C., Yellow powder (from n-Hexane-chloroform),
$[α]^{25}/_D$ = +26.5($CH_3OH$, c = 0.2), $C_{30}H_{37}N_4O_5Cl.½H_2O$, MS $[M + H]^+$ = 569,
Anal. (C, H, N): Found (calcd.) 62.69, 6.58, 9.73 (62.33, 6.63, 9.69),
$IRv^{MAX}/_{KBr}$ (cm$^{-1}$): 1725, 1650, 1595, 1515.
$^1$H-NMR (δppm) in $CDCl_3$: 0.92(3H, t, J=7Hz), 1.12(3H, t, J=7Hz), 1.33(3H, t,

TABLE 3-continued (Spectral Data of 17-O-Acyl-21-amide Compounds)

J=8Hz), 1.64(2H, sextet, J=7Hz), 2.16–2.35(3H, m), 2.25(6H, s), 2.38–2.59(3H, m), 2.90–3.07(2H, m), 3.21–3.32(1H, m), 3.39–3.50(1H, m), 4.96(1H, d, J=19Hz), 5.07(1H, d, J=19Hz), 5.31–5.60(1H, br), 5.45(1H, d, J=12Hz), 5.50(1H, d, J=12Hz), 7.46(1H, br-t, J=5Hz), 7.47(1H, s), 7.60(1H, dd, J=2, 9Hz), 7.68(1H, d, J=2Hz), 7.89(1H, d, J=9Hz).

$C_5$ mp 139–144° C., Yellow powder (from n-Hexane-chloroform),
$[\alpha]^{25}/_D$ = +20.5($CH_3OH$, c = 0.2), $C_{30}H_{37}N_4O_5ClS \cdot \frac{1}{2}H_2O$, MS $[M + H]^+$ = 601,
Anal. (C, H, N): Found (calcd.) 59.28, 6.31, 9.01 (59.05, 6.28, 9.18),
$IRv^{MAX}/_{KBr}$ ($cm^{-1}$): 1725, 1650, 1600, 1515.
$^1$H-NMR (δppm) in $CDCl_3$: 1.10(3H, t, J=7Hz), 1.34(3H, t, J=8Hz), 2.09(3H, s), 2.23–2.35(1H, m), 2.31(6H, s), 2.44–2.68(5H, m), 2.70–2.80(2H, m), 2.93–3.09(2H, m), 3.24–3.35(1H, m), 3.43–3.57(1H, m), 5.00(1H, d, J=19Hz), 5.09(1H, d, J=19Hz), 5.51(2H, s), 7.51(1H, s), 7.52(1H, br-t, J=5Hz), 7.62(1H, dd, J=2, 9Hz), 7.74(1H, d, J=2Hz), 7.93(1H, d, J=9Hz).

$C_6$ mp 149–151° C., Pale yellow needles (from n-Hexane-chloroform),
$[\alpha]^{25}/_D$ = +18.5($CH_3OH$, c = 0.2), $C_{30}H_{37}N_4O_5BrS$, MS $[M + H]^+$ = 645,
Anal. (C, H, N): Found (calcd.) 55.95, 5.70, 8.50 (55.81, 5.78, 8.68),
$IRv^{MAX}/_{KBr}$ ($cm^{-1}$): 1725, 1650, 1610, 1515.
$^1$H-NMR (δppm) in $CDCl_3$: 1.09(3H, t, J=7Hz), 1.36(3H, t, J=8Hz), 2.10(3H, s), 2.22–2.35(1H, m), 2.25(6H, s), 2.38–2.55(3H, m), 2.57–2.68(2H, m), 2.71–2.81(2H, m), 2.97–3.10(2H, m), 3.24–3.34(1H, m), 3.38–3.50(1H, m), 4.98–5.34(1H, br), 5.05(1H, d, J=19Hz), 5.13(1H, d, J=19Hz), 5.49(1H, d, J=12Hz); 5.57(1H, d, J=12Hz), 7.40(1H, br-t, J=6Hz), 7.53(1H, s), 7.77(1H, dd, J=2, 9Hz), 7.90(1H, d, J=9Hz), 8.00(1H, d, J=2Hz).

$C_7$ mp 130–134° C., Yellow powder (from n-Hexane-chloroform),
$[\alpha]^{25}/_D$ = +21.5($CH_3OH$, c = 0.2), $C_{31}H_{40}N_4O_5S$, MS $[M + H]^+$ = 581,
Anal. (C, H, N): Found (calcd.) 63.88, 7.02, 9.43 (64.11, 6.94, 9.65),
$IRv^{MAX}/_{KBr}$ ($cm^{-1}$): 1725, 1650, 1600, 1515.
$^1$H-NMR (δppm) in $CDCl_3$: 1.09(3H, t, J=7Hz), 1.32(3H, t, J=8Hz), 2.09(3H, s), 2.20–2.36(1H, m), 2.26(6H, s), 2.41–2.55(3H, m), 2.54(3H, s), 2.57–2.67(2H, m), 2.71–2.81(2H, m), 2.93–3.09(2H, m), 3.25–3.35(1H, m), 3.41–3.52(1H, m), 4.99(1H, d, J=19Hz), 5.97(1H, d, J=19Hz), 5.50(1H, d, J=12Hz), 5.54(1H, d, J=12Hz), 7.44(1H, br-t, J=6Hz), 7.51(1H, dd, J=2, 8Hz), 7.52(1H, s), 7.55(1H, br-s), 7.94(1H, d, J=8Hz).

$C_8$ mp 164–166° C., Pale yellow powder (from n-Hexane-chloroform),
$[\alpha]^{25}/_D$ = +24.0($CH_3OH$, c = 0.2), $C_{29}H_{35}N_4O_5F \cdot 2H_2O$, MS $[M + H]^+$ = 539,
Anal. (C, H, N): Found (calcd.) 60.24, 6.80, 9.84 (60.61, 6.84, 9.75),
$IRv^{MAX}/_{KBr}$ ($cm^{-1}$): 1725, 1650, 1595, 1510.
$^1$H-NMR (δppm) in $CDCl_3$: 1.08(3H, t, J=7Hz), 1.13(3H, t, J=7Hz), 1.36(3H, t, J=8Hz), 2.24–2.63(6H, m), 2.30(6H, s), 3.02–3.20(2H, m), 3.25–3.55(2H, m), 5.07(1H, d, J=19Hz), 5.14(1H, d, J=19Hz), 5.21–5.41(1H, br), 5.51(2H, br-s), 7.31(1H, ddd, J=2, 9, 10Hz), 7.41(1H, br-t, J=5Hz), 7.55(1H, s), 7.69(1H, dd, J=2, 10Hz), 7.93(1H, dd, J=6, 9Hz).

$C_9$ mp 134–137° C., Pale yellow powder (from n-Hexane-chloroform),
$[\alpha]^{25}/_D$ = +22.0($CH_3OH$, c = 0.2), $C_{30}H_{37}N_4O_5F \cdot \frac{1}{2}H_2O$, MS $[M + H]^+$ = 553,
Anal. (C, H, N): Found (calcd.) 62.06, 6.85, 9.70 (62.16, 6.96, 9.67),
$IRv^{MAX}/_{KBr}$ ($cm^{-1}$): 1725, 1650, 1595, 1510.
$^1$H-NMR (δppm) in $CDCl_3$: 0.93(3H, t, J=7Hz), 1.09(3H, t, J=7Hz), 1.36(3H, t, J=8Hz), 1.65(2H, sextet, J=7Hz), 2.20–2.36(3H, m), 2.25(6H, s), 2.39–2.53(3H, m), 3.02–3.17(2H, m), 3.25–3.35(1H, m), 3.38–3.49(1H, m), 5.05(1H, d, J=19Hz), 5.12(1H, d, J=19Hz), 5.22–5.40(1H, br), 5.47(1H, d, J=12Hz), 5.53((1H, d, J=12Hz), 7.30(1H, ddd, J=3, 9, 10Hz), 7.38(1H, br-t, J=5Hz), 7.53(1H, s), 7.67(1H, dd, J=3, 10Hz), 7.91(1H, dd, J=6, 9Hz).

$C_{10}$ mp 135–138° C., Pale yellow powder (from n-Hexane-chloroform),
$[\alpha]^{25}/_D$ = +16.5($CH_3OH$, c = 0.2), $C_{30}H_{37}N_4O_5FS \cdot \frac{1}{2}H_2O$, MS $[M + H]^+$ = 585
Anal. (C, H, N): Found (calcd.) 58.74, 6.48, 9.21 (58.90, 6.59, 9.16),
$IRv^{MAX}/_{KBr}$ ($cm^{-1}$): 1730, 1650, 1595, 1510.
$^1$H-NMR (δppm) in $CDCl_3$: 1.09(3H, t, J=7Hz), 1.36(3H, t, J=8Hz), 2.10(3H, s), 2.20–2.36(1H, m), 2.25(6H, s), 2.40–2.54(3H, m), 2.58–2.68(2H, m), 2.72–2.82(2H, m), 3.04–3.18(2H, m), 3.25–3.36(1H, m), 3.39–3.50(1H, m), 4.99–5.31(1H, br), 5.06(1H, d, J=19Hz), 5.14(1H, d, J=19Hz), 5.49(1H, d, J=12Hz), 5.58(1H, d, J=12Hz), 7.31(1H, ddd, J=3, 9, 10Hz), 7.39(1H, br-t, J=5Hz), 7.55(1H, s), 7.68(1H, dd, J=3, 10Hz), 7.93(1H, dd, J=6, 9Hz).

TABLE 3-continued (Spectral Data of 17-O-Acyl-21-amide Compounds)

$C_{11}$ mp 180–182° C., Pale yellow powder (from n-Hexane-chloroform),
$[\alpha]^{25}/_D$ = −59.5(CH$_3$OH, c = 0.2), C$_{34}$H$_{37}$N$_4$O$_6$F.H$_2$O, MS [M + H]$^+$ = 617
Anal. (C, H, N): Found (calcd.) 64.34, 6.40, 8.98 (64.34, 6.19, 8.83),
IRv$^{MAX}$/$_{KBr}$ (cm$^{-1}$): 1700, 1650, 1600, 1510
$^1$H-NMR (δppm) in CDCl$_3$: 1.12(3H, t, J=7Hz), 1.34(3H, t, J=8Hz), 2.18(6H, s), 2.29–
2.44(3H, m), 2.47–2.59(1H, m), 2.99–3.22(3H, m), 3.30–3.42(1H, m), 5.03(1H, d,
J=19Hz), 5.12(1H, d, J=19Hz), 5.58–5.93(1H, br), 5.73(1H, d, J=12Hz), 5.81(1H,
d, J=12Hz), 6.82(2H, d, J=9Hz), 7.22–7.28(1H, m), 7.51(1H, br-t, J=5Hz), 7.57(1H,
1H, s), 7.63(1H, dd, J=3, 10Hz), 7.85(1H, dd, J=6, 9Hz), 7.96(2H, d, J=9Hz).

$C_{12}$ mp 131–133° C., Pale yellow powder (from n-Hexane-chloroform),
$[\alpha]^{25}/_D$ = +25.5(CH$_3$OH, c = 0.2), C$_{30}$H$_{37}$N$_4$O$_5$ClS.H$_2$O, MS [M + H]$^+$ = 601,
Anal. (C, H, N): Found (calcd.) 57.80, 6.05, 8.91 (58.20, 6.35, 9.05)
IRv$^{MAX}$/$_{KBr}$ (cm$^{-1}$): 1730, 1650, 1605, 1515.
$^1$H-NMR (δppm) in CDCl$_3$: 1.09(3H, t, J=7Hz), 1.37(3H, t, J=8Hz), 2.10(3H,
s), 2.22–2.36(1H, m), 2.26(6H, s), 2.40–2.54(3H, m), 2.56–2.68(2H, m), 2.70–
2.81(2R, m), 3.02–3.18(2H, m), 3.25–3.35(1H, m), 3.40–3.52(1H, m), 4.97–5.35(1H,
br), 5.05(1H, d, J=19Hz), 5.13(1H, d, J=19Hz), 5.49(1H, d, J=11Hz), 5.57(1H,
d, J=11Hz), 7.42(1H, br-t, J=6Hz), 7.46(1H, dd, J=2, 9Hz), 7.54(1H, s),
7.85(1H, d, J=9Hz), 8.02(1H, d, J=2Hz).

$C_{13}$ mp 168–170° C., Yellow powder (from n-Hexane-chloroform),
$[\alpha]^{25}/_D$ = +24.0(CH$_3$OH, c = 0.2), C$_{29}$H$_{34}$N$_4$O$_5$F$_2$.H$_2$O, MS [M + H]$^+$ = 557,
Anal. (C, H, N): Found (calcd.) 60.91, 6.22, 9.75 (60.62, 6.31, 9.75),
IRv$^{MAX}$/$_{KBr}$ (cm$^{-1}$): 1725, 1655, 1600, 1515.
$^1$H-NMR (δppm) in CDCl$_3$: 1.07(3H, t, J=7Hz), 1.13(3H, t, J=7Hz), 2.36(3H, t,
J=8Hz), 2.18–2.52(6H, m), 2.24(6H, s), 3.07(2H, q, J=8Hz), 3.25–3.36(1H, m),
3.38–3.49(1H, m), 5.06–5.38(1H, br), 5.10(1H, d, J=19Hz), 5.16(1H, d, J=19Hz),
5.48(1H, d, J=12Hz), 5.56(1H, d, J=12Hz), 7.36(1H, br-t, J=5Hz), 7.55(1H, s),
7.69(1H, d, J=8, 11Hz), 7.86(1H, d, J=8, 11Hz).

$C_{14}$ mp 160–162° C., Yellow powder (from n-Hexane-chloroform),
$[\alpha]^{25}/_D$ = +21.5(CH$_3$OH, c = 0.2), C$_{30}$H$_{36}$N$_4$O$_5$F$_2$.½H$_2$O, MS [M + H]$^+$ = 571,
Anal. (C, H, N): Found (calcd.) 61.73, 6.53, 9.75 (62.16, 6.43, 9.67),
IRv$^{MAX}$/$_{KBr}$ (cm$^{-1}$): 1720, 1655, 1600, 1520.
$^1$H-NMR (δppm) in CDCl$_3$: 0.93(3H, t, J=7Hz), 1.07(3H, t, J=7Hz), 1.36(3H, t, J=8Hz),
1.65(2H, sextet, J=7Hz), 2.16–2.36(3H, m), 2.24(6H, s), 2.38–2.52(3H, m), 3.07(2H,
q, J=8Hz), 3.25–3.36(1H, m), 3.37–3.48(1H, m), 5.05–5.34(1H, br), 5.10(1H, d,
J=19Hz), 5.16(1H, d, J=19Hz), 5.47(1H, d, J=12Hz), 5.57(1H, d, J=12Hz), 7.35(1H,
br-t, J=5Hz), 7.55(1H, s), 7.70(1H, dd, J=8, 11Hz), 7.86(1H, dd, J=8, 11Hz).

$C_{15}$ mp 119–125° C., Yellow needles (from n-Hexane-chloroform),
$[\alpha]^{25}/_D$ = +22.0(CH$_3$OH, c = 0.2), C$_{30}$H$_{36}$N$_4$O$_5$F$_2$S.H$_2$O, MS [M + H]$^+$ = 603,
Anal. (C, H, N): Found (calcd.) 57.83, 6.03, 9.08 (58.05, 6.17, 9.03),
IRv$^{MAX}$/$_{KBr}$ (cm$^{-1}$): 1725, 1650, 1600, 1515.
$^1$H-NMR (δppm) in CDCl$_3$: 1.08(3H, t, J=7Hz), 1.36(3H, t, J=8Hz), 2.10(3H, s), 2.20–
2.34(2H, m), 2.25(6H, s), 2.40–2.54(3H, m), 2.58–2.70(2H, m), 2.71–2.83(2H, m),
3.07(2H, q, J=8Hz), 3.26–3.37(1H, m), 3.40–3.52(1H, m), 5.08(1H, d, J=19Hz),
5.15(1H, d, J=19Hz), 5.49(1H, d, J=12Hz), 5.60(1H, d, J=12Hz), 7.43(1H, br-t,
J=5Hz), 7.55(1H, s), 7.67(1H, dd, J=8, 11Hz), 7.83(1H, dd, J=8, 11Hz).

$C_{16}$ mp 175–178° C., Colorless needles (from n-hexane-chloroform)
$[\alpha]^{25}/_D$ = −57.0(CH$_3$OH, c = 0.2), C$_{34}$H$_{37}$N$_4$O$_6$F$_2$.½H$_2$O, MS [M + H]$^+$ = 635,
Anal. (C, H, N): Found (calcd.) 63.74, 5.79, 8.93 (63.44, 5.79, 8.70),
IRv$^{MAX}$/$_{KBr}$ (cm$^{-1}$): 1695, 1650, 1600, 1510.
$^1$H-NMR (δppm) in CDCl$_3$: 1.10(3H, t, J=7Hz), 1.35(3H, t, J=8Hz), 2.19(6H,
s), 2.26–2.55(4H, m), 3.05(2H, q, J=8Hz), 3.14–3.25(1H, m), 3.30–3.42(1H, m),
5.08(1H, d, J=19Hz), 5.15(1H, d, J=19Hz), 5.55–5.90(1H, br), 5.70(1H, d, J=
12Hz), 5.84(1H, d, J=12Hz), 6.84(2H, d, J=9Hz), 7.48(1H, br-t, J=5Hz), 7.55(1H,
s), 7.65(1H, dd, J=8, 11Hz), 7.82(1H, dd, J=8, 11Hz), 7.97(2H, d, J=9Hz).

$C_{17}$ mp 153–156° C., Yellow powder (from n-hexane-chloroform)
$[\alpha]^{25}/_D$ = +34.5(CH$_3$OH, c = 0.2), C$_{29}$H$_{34}$N$_4$O$_5$Cl$_2$.½H$_2$O, MS [M + H]$^+$ = 589,
Anal. (C, H, N): Found (calcd.) 58.12, 5.74, 9.35 (58.20, 5.89, 9.36),
IRv$^{MAX}$/$_{KBr}$ (cm$^{-1}$): 1725, 1650, 1600, 1515.
$^1$H-NMR (δppm) in CDCl$_3$: 1.11(3H, t, J=7Hz), 1.12(3H, t, J=7Hz), 1.38(3H, t, J=
8Hz), 2.19–2.38(3H, m), 2.27(6H, s), 2.40–2.58(3H, m), 2.96–3.14(2H, m), 3.21–
3.32(1H, m), 3.40–3.51(1H, m), 4.99(1H, d, J=19Hz), 5.08(1H, d, J=19Hz), 5.45(1H,
d, J=12Hz), 5.49(1H, d, J=12Hz), 7.46(1H, s), 7.49(1H, br-t, J=5Hz),

TABLE 3-continued (Spectral Data of 17-O-Acyl-21-amide Compounds)

7.89(1H, s), 8.05(1H, s).

$C_{18}$ mp 142–147° C., Yellow powder (from n-hexane-chloroform)
$[\alpha]^{25}/_D$ = +31.5(CH$_3$OH, c = 0.2),
$C_{30}H_{36}N_4O_5Cl_2$·½$H_2O$, MS [M + H]$^+$ = 603,
Anal. (C, H, N): Found (calcd.) 58.97, 5.95, 9.06 (58.82, 6.09, 9.15),
IR$\nu^{MAX}/_{KBr}$ (cm$^{-1}$): 1725, 1650, 1600, 1515
$^1$H-NMR (δppm) in CDCl$_3$: 0.92(3H, t, J=7Hz), 1.11(3H, t, J=7Hz), 1.38(3H, t, J=8Hz), 1.64(2H, sextet, J=7Hz), 2.18–2.35(3H, m), 2.26(6H, s), 2.39–2.56(3H, m), 2.98–3.14(2H, m), 3.21–3.32(1H, m), 3.38–3.52(1H, m), 5.00(1H, d, J=19Hz), 5.09(1H, d, J=19Hz), 5.48(2H, s), 7.45(1H, br-t, J=5Hz), 7.47(1H, s), 7.92(1H, s), 8.07(1H, s).

$C_{19}$ mp 139–142° C., Yellow needles (from n-hexane-chloroform)
$[\alpha]^{25}/_D$ = +27.5(CH$_3$OH, c = 0.2), $C_{30}H_{36}N_4O_5Cl_2S$·½$H_2O$, MS [M + H]$^+$ = 635,
Anal. (C, H, N): Found (calcd.) 55.94, 5.69, 8.79 (55.90, 5.79, 8.69),
IR$\nu^{MAX}/_{KBr}$ (cm$^{-1}$): 1725, 1650, 1600, 1515.
$^1$H-NMR (δppm) in CDCl$_3$: 1.09(3H, t, J=7Hz), 1.38(3H, t, J=8Hz), 2.09(3H, s), 2.21–2.37(1H, m), 2.29(6H, s), 2.43–2.67(5H, m), 2.70–2.81(2H, m), 2.99–3.16(2H, m), 3.24–3.35(1H, m), 3.42–3.55(1H, m), 5.03(1H, d, J=19Hz), 5.11(1H, d, J=19Hz), 5.49(1H, d, J=12Hz), 5.54(1H, d, J=12Hz), 7.49(1H, br-t, J=6Hz), 7.50(1H, s), 7.96(1H, s), 8.11(1H, s).

$C_{20}$ mp 112–117° C., Pale yellow powder (from n-hexane-chloroform)
$[\alpha]^{25}/_D$ = +28.5(CH$_3$OH, c = 0.2), $C_{30}H_{37}N_4O_6F$·½$H_2O$, MS [M + H]$^+$ = 569,
Anal. (C, H, N): Found (calcd.) 60.15, 6.78, 9.40 (60.49, 6.77, 9.41),
IR$\nu^{MAX}/_{KBr}$ (cm$^{-1}$): 1725, 1650, 1595, 1515.
$^1$H-NMR (δppm) in CDCl$_3$: 1.12(3H, t, J=7Hz), 1.13(3H, t, J=7Hz), 1.31(3H, t, J=8Hz), 2.21–2.63(6H, m), 2.28(6H, s), 2.88–3.08(2H, m), 3.18–3.30(1H, m), 3.40–3.52(1H, m), 4.00(3H, s), 4.89(1H, d, J=19Hz), 5.02(1H, d, J=19Hz), 5.41(1H, d, J=12Hz), 5.50(1H, d, J=12Hz), 6.89(1H, d, J=9Hz), 7.40(1H, s), 7.46(1H, br-t, J=6Hz), 7.57(1H, d, J=12Hz).

$C_{21}$ mp 109–113° C., Pale yellow powder (from n-hexane-chloroform)
$[\alpha]^{25}/_D$ = +29.5(CH$_3$OH, c = 0.2), $C_{31}H_{39}N_4O_6F$·2$H_2O$, MS [M + H]$^+$ = 583,
Anal. (C, H, N): Found (calcd.) 60.09, 6.99, 9.29 (60.18, 7.01, 9.06),
IR$\nu^{MAX}/_{KBr}$ (cm$^{-1}$): 1725, 1650, 1595, 1510.
$^1$H-NMR (δppm) in CDCl$_3$: 0.92(3H, t, J=7Hz), 1.13(3H, t, J=7Hz), 1.31(3H, t, J=8Hz), 1.63(2H, sextet, J=7Hz), 2.18–2.37(3H, m), 2.28(6H, s), 2.39–2.63(3H, m), 2.87–3.07(2H, m), 3.17–3.30(1H, m), 3.41–3.53(1H, m), 4.00(3H, s), 4.89(1H, d, J=19Hz), 5.02(1H, d, J=19Hz), 5.34–5.57(1H, br), 5.40(1H, d, J=12Hz), 5.49(1H, d, J=12Hz), 6.89(1H, d, J=9Hz), 7.40(1H, s), 7.46(1H, br-t, J=6Hz), 7.57(1H, d, J=12Hz).

$C_{22}$ mp 125–129° C., Pale yellow powder (from n-hexane-chloroform)
$[\alpha]^{25}/_D$ = +22.0(CH$_3$OH, c = 0.2), $C_{31}H_{39}N_4O_6FS$·½$H_2O$, MS [M + H]$^+$ = 615,
Anal. (C, H, N): Found (calcd.) 59.82, 6.40, 9.02 (59.89, 6.60, 8.73),
IR$\nu^{MAX}/_{KBr}$ (cm$^{-1}$): 1725, 1650, 1600, 1510.
$^1$H-NMR (δppm) in CDCl$_3$: 1.11(3H, t, J=7Hz), 1.33(3H, t, J=8Hz), 2.09(3H, s), 2.22–2.36(1H, m), 2.26(6H, s), 2.39–2.69(5H, m), 2.71–2.80(2H, m), 2.94–3.10(2H, m), 3.21–3.34(1H, m), 3.39–3.15(1H, m), 4.04(3H, s), 4.93–5.38(1H, br), 4.97(1H, d, J=19Hz), 5.07(1H, d, J=19Hz), 5.50(2H, s), 7.01(1H, d, J=9Hz), 7.38(1H, br-t, J=6Hz), 7.44(1H, s), 7.64(1H, d, J=12Hz).

$C_{23}$ mp 164–165° C., Pale yellow powder (from n-hexane-chloroform)
$[\alpha]^{25}/_D$ = +24.5(CH$_3$OH, c = 0.2), $C_{30}H_{37}N_4O_6F$·½$H_2O$, MS [M + H]$^+$ = 553,
Anal. (C, H, N): Found (calcd.) 61.88, 6.85, 9.71 (62.16, 6.96, 9.67),
IR$\nu^{MAX}/_{KBr}$ (cm$^{-1}$): 1725, 1650, 1595, 1510.
$^1$H-NMR (δppm) in CDCl$_3$: 1.09(3H, t, J=7Hz), 1.13(3H, t, J=7Hz), 1.36(3H, t, J=8Hz), 2.19–2.57(6H, m), 2.25(6H, s), 2.48(3H, s), 2.99–3.16(2H, m), 3.23–3.34(1H, m), 3.38–3.49(1H, m), 5.02(1H, d, J=19Hz), 5.10(1H, d, J=19Hz), 5.49(2H, s), 7.38(1H, br-t, J=5Hz), 7.49(1H, s), 7.58(1H, d, J=11Hz), 7.67(1H, d, J=8Hz).

$C_{24}$ mp 148–154° C., Pale yellow needles (from n-hexane-chloroform)
$[\alpha]^{25}/_D$ = +24.0(CH$_3$OH, c = 0.2), $C_{31}H_{39}N_4O_6F$·½$H_2O$, MS [M + H]$^+$ = 567,
Anal. (C, H, N): Found (calcd.) 64.28, 7.07, 9.65 (64.68, 7.00, 9.73),
IR$\nu^{MAX}/_{KBr}$ (cm$^{-1}$): 1725, 1650, 1600, 1510.
$^1$H-NMR (δppm) in CDCl$_3$: 0.93(3H, t, J=7Hz), 1.09(3H, t, J=7Hz), 1.36(3H, t, J=8Hz), 1.64(2H, sextet, J=7Hz), 2.19–2.35(3H, m), 2.24(6H, s), 2.38–2.54(3H, m), 2.48(3H, s), 2.99–3.16(2H, m), 3.23–3.34(1H, m), 3.38–3.50(1H, m),

TABLE 3-continued (Spectral Data of 17-O-Acyl-21-amide Compounds)

5.02(1H, d, J=19Hz), 5.10(1H, d, J=19Hz), 5.21–5.42(1H, br), 5.47(1H, d, J=
12Hz), 5.51(1H, d, J=12Hz), 7.38(1H, br-t, J=5Hz), 7.49(1H, s), 7.58(1H, d,
J=11Hz), 7.68(1H, d, J=8Hz).

$C_{25}$ mp 107–121° C., Yellow needles (from n-hexane-chloroform)
$[\alpha]^{25}/_D$ = +54.0(CH$_3$OH, c = 0.2), $C_{31}H_{39}N_4O_5FS.2H_2O$, MS [M + H]$^+$ = 599,
Anal. (C, H, N): Found (calcd.) 60.75, 6.67, 9.15 (60.55, 6.83, 8.83),
IRv$^{MAX}/_{KBr}$ (cm$^{-1}$): 1725, 1650, 1595, 1510.
$^1$H-NMR (δppm) in CDCl$_3$: 1.10(3H, t, J=7Hz), 1.36(3H, t, J=8Hz), 2.09(3H,
s), 2.22–2.35(1H, m), 2.28(6H, s), 2.40–2.66(5H, m), 2.46(3H, s), 2.72–2.81(2H,
m), 2.97–3.14(2H, m), 3.24–3.34(1H, m), 3.42–3.54(1H, m), 4.98(1H, d, J=
19Hz), 5.07(1H, d, J=19Hz), 5.51(2H, s), 7.47(1H, s), 7.48(1H, br-t, J=5Hz),
7.54(1H, d, J=11Hz), 7.63(1H, d, J=8Hz).

$C_{26}$ mp 189–192° C., Pale yellow powder (from n-hexane-chloroform)
$[\alpha]^{25}/_D$ = −59.0(CH$_3$OH, c = 0.2), $C_{35}H_{39}N_4O_6F.H_2O$, MS [M + H]$^+$ = 631,
Anal. (C, H, N): Found (calcd.) 64.43, 6.57, 8.73 (64.80, 6.37, 8.64),
IRv$^{MAX}/_{KBr}$ (cm$^{-1}$): 1700, 1650, 1605, 1510.
$^1$H-NMR (δppm) in CDCl$_3$: 1.12(3H, t, J=7Hz), 1.34(3H, 6, J=8Hz), 2.17(6H,
s), 2.28–2.42(3H, m), 2.45(3H, s), 2.48–2.60(1H, m), 2.96–3.18(3H, m), 3.28–
3.39(1H, m), 4.98(1H, d, J=19Hz), 5.09(1H, d, J=19Hz), 5.52–5.98(1H, br), 5.74
(1H, d, J=12Hz), 5.78(1H, d, J=12Hz), 6.82(2H, d, J=9Hz), 7.48–7.55(3H, m),
7.60(1H, d, J=8Hz), 7.95(1H, d, J=9Hz).

$C_{27}$ mp 82–87° C., Yellow prisms (from n-hexane-chloroform)
$[\alpha]^{25}/_D$ = +24.0(CH$_3$OH, c = 0.2), $C_{33}H_{44}N_4O_8.H_2O$, MS [M + H]$^+$ = 625,
Anal. (C, H, N): Found (calcd.) 61.85, 7.12, 8.81 (61.67, 7.21, 8.72),
IRv$^{MAX}/_{KBr}$ (cm$^{-1}$): 1730, 1650, 1620, 1510.
$^1$H-NMR (δppm) in CDCl$_3$: 1.08(3H, t, J=7Hz), 1.12(3H, t, J=7Hz), 1.30(3H,
t, J=8Hz), 2.25–2.41(3H, m), 2.35(6H, s), 2.43–2.66(3H, m), 2.91–3.07(2H, m),
3.27–3.37(1H, m), 3.39(3H, s), 3.46–3.63(3H, m), 3.83–3.93(2H, m), 4.99(1H, d,
J=19Hz), 5.08(1H, d, J=19Hz), 5.27–5.62(1H, br), 5.38(1H, d, J=7Hz), 5.41(1H,
d, J=7Hz), 5.46(1H, d, J=12Hz), 5.50(1H, d, J=12Hz), 7.34(1H, d, J=3Hz), 7.39(1H,
dd, J=3, 9Hz), 7.44–7.55(2H, s, br-t), 7.96(1H, d, J=9Hz)

$C_{28}$ mp 214–215° C., Pale yellow powder (from n-hexane-chloroform)
$[\alpha]^{25}/_D$ = +34.0(CH$_3$OH, c = 0.2), $C_{29}H_{36}N_4O_6$, MS [M + H]$^+$ = 537,
Anal. (C, H, N): Found (calcd.) 64.67, 6.69, 10.22 (64.91, 6.76, 10.44),
IRv$^{MAX}/_{KBr}$ (cm$^{-1}$): 1720, 1645, 1620, 1585.
$^1$H-NMR (δppm) in DMSO-d$_6$: 0.87(3H, t, J=7Hz), 1.05(3H, t, J=8Hz), 1.31(3H,
t, J=8Hz), 2.08–2.24(2H, m), 2.27(2H, q, J=8Hz), 2.74(6H, s), 2.99–3.15(4H,
m), 3.22–3.54(2H, m), 5.25(2H, s), 5.31(1H, d, J=11Hz), 5.37(1H, d, J=11Hz),
6.28(1H, s), 7.38–7.47(3H, m), 8.02(1H, d, J=10Hz), 8.30(1H, br-t, J=6Hz),
9.43–9.88(1H, br), 10.36(1H, s).

$C_{29}$ mp 78–82° C., Yellow needles (from n-hexane-chloroform)
$[\alpha]^{25}/_D$ = +22.5(CH$_3$OH, c = 0.2), $C_{34}H_{46}N_4O_8.\frac{1}{2}H_2O$, MS [M + H]$^+$ = 639,
Anal. (C, H, N): Found (calcd.) 61.61, 7.03, 8.38 (61.34, 7.42, 8.42),
IRv$^{MAX}/_{KBr}$ (cm$^{-1}$): 1725, 1620, 1585, 1510.
$^1$H-NMR (δppm) in CDCl$_3$: 0.93(3H, t, J=7Hz), 1.08(3H, t, J=7Hz), 1.30(3H, t, J=8Hz),
1.64(2H, sext, J=7Hz), 2.23–2.38(3H, m), 2.34(6H, s), 2.43–2.64(3H, m), 2.89–
3.08(2H, m), 3.25–3.36(1H, m), 3.39(3H, s), 3.45–3.63(3H, m), 3.83–3.93(2H, m),
4.98(1H, d, J=19Hz), 5.08(1H, d, J=19Hz), 5.30–5.58(1H, br), 5.37(1H, d, J=
7Hz), 5.41(1H, d, J=7Hz), 5.46(1H, d, J=12Hz), 5.49(1H, d, J=12Hz), 7.34(1H, d,
J=3Hz), 7.39(1H, dd, J=3, 9Hz), 7.44–7.52(2H, s, br-t), 7.95(1H, d, J=9Hz).

$C_{30}$ mp 218–219° C., Colorless powder (from n-hexane-chloroform)
$[\alpha]^{25}/_D$ = +32.5(CH$_3$OH, c = 0.2), $C_{30}H_{38}N_4O_6$, MS [M + H]$^+$ = 551,
Anal. (C, H, N): Found (calcd.) 65.34, 6.99, 10.04 (65.44, 6.96, 10.17),
IRv$^{MAX}/_{KBr}$ (cm$^{-1}$): 1715, 1645, 1620, 1585.
$^1$H-NMR (δppm) in DMSO-d$_6$: 0.87(3H, t, J=7Hz), 0.90(3H, t, J=7Hz), 1.30(3H,
t, J=8Hz), 1.55(2H, sextet, J=7Hz), 2.12(6H, s), 2.25–2.32(6H, m), 3.02–3.25(4H,
m), 5.26(2H, s), 5.29(1H, d, J=11Hz), 5.37(1H, d, J=11Hz), 6.28(1H, s),
7.37(1H, s), 7.38–7.45(2H, m), 7.78(1H, br-t, J=6Hz), 8.04(1H, d, J=10Hz),
10.29(1H, br-s).

$C_{31}$ mp 84–90° C., Pale yellow powder (from n-hexane-chloroform)
$[\alpha]^{25}/_D$ = +18.0(CH$_3$OH, c = 0.2), $C_{34}H_{46}N_4O_8S.H_2O$, MS [M + H]$^+$ = 671,
Anal. (C, H, N): Found (calcd.) 59.33, 6.77, 7.96 (59.28, 7.02, 8.13),
IRv$^{MAX}/_{KBr}$ (cm$^{-1}$): 1725, 1620, 1585, 1510.

TABLE 3-continued (Spectral Data of 17-O-Acyl-21-amide Compounds)

$^1$H-NMR (δppm) in CDCl$_3$: 1.07(3H, t, J=7Hz), 1.31(3H, t, J=8Hz), 2.09(3H, s), 2.24–2.41(1H, m), 2.36(6H, s), 2.42–2.68(5H, m), 2.71–2.80(2H, m), 2.93–3.07(2H, m), 3.27–3.41(1H, m), 3.39(3H, s), 3.49–3.61(3H, m), 3.83–3.92(2H, m), 5.00(1H, d, J=19Hz), 5.10(1H, d, J=19Hz), 5.22–5.60(1H, br), 5.38(1H, d, J=7Hz), 5.42(1H, d, J=7Hz), 5.52(2H, s), 7.37(1H, d, J=3Hz), 7.41(1H, dd, J=3, 9Hz), 7.44–7.54(2H, br-m), 7.97(1H, d, J=9Hz).

$C_{32}$ mp 172–175° C., Pale yellow powder (from n-hexane-chloroform)
$[α]^{25}/_D$ = +25.0(CH$_3$OH, c = 0.2), C$_{30}$H$_{38}$N$_4$O$_6$S, MS [M + H]$^+$ = 583,
Anal. (C, H, N): Found (calcd.) 61.62, 6.52, 9.44 (61.84, 6.57, 9.61),
IRν$^{MAX}$/$_{KBr}$ (cm$^{-1}$): 1725, 1645, 1620, 1585.
$^1$H-NMR (δppm) in DMSO-d$_6$: 0.87(3H, t, J=7Hz), 1.30(3H, t, J=8Hz), 2.02–2.32 (4H, m), 2.07(3H, s), 2.13(6H, s), 2.52–2.59(2H, m), 2.64–2.72(2H, m), 3.00–3.26(4H, m), 5.26(2H, s), 5.34(1H, d, J=11Hz), 5.42(1H, d, J=11Hz), 6.22(1H, s), 7.34–7.48(3H, m), 7.79(1H, br-t, J=6Hz), 8.04(1H, d, J=10Hz), 10.30(1H, br).

$C_{33}$ mp 78–86° C., Yellow needles (from n-Hexane-chloroform)
C$_{34}$H$_{44}$N$_4$O$_8$·½H$_2$O, MS [M + H]$^+$ = 637,
Anal. (C, H, N): Found (calcd.) 63.02, 7.02, 8.67 (63.24, 7.02, 8.68),
IRν$^{MAX}$/$_{KBr}$ (cm$^{-1}$): 1710, 1620, 1585, 1510.
$^1$H-NMR (δppm) in CDCl$_3$: 1.08(3H, t, J=7Hz), 1.31(3H, t, J=8Hz), 1.83(3H, dd, J=2, 7Hz), 2.25(6H, s), 2.26–2.37(1H, m), 2.39–2.53(3H, m), 2.94–3.08(2H, m), 3.21–3.47(1H, m), 3.39(3H, s), 3.54–3.61(2H, m), 3.84–3.91(2H, m), 5.04(1H, d, J=19Hz), 5.12(1H, d, J=19Hz), 5.39(1H, d, J=7Hz), 5.42(1H, d, J=7Hz), 5.53(1H, d, J=12Hz), 5.61(1H, d, J=12Hz), 5.80–5.88(1H, m), 6.98(1H, dq, J=7, 14Hz), 7.32–7.55(4H, m), 8.00(1H, d, J=9Hz).

$C_{34}$

Yellow powder (from n-Hexane-chloroform)
C$_{30}$H$_{36}$N$_4$O$_6$, MS [M + H]$^+$ = 549,
IRν$^{MAX}$/$_{KBr}$ (cm$^{-1}$): 1705, 1675, 1645, 1590, 1510.
$^1$H-NMR (δppm) in DMSO-d$_6$: 0.88(3H, t, J=7Hz), 1.31(3H, t, J=8Hz), 1.84(3H, dd, J=2, 7Hz), 2.08–2.26(2H, m), 2.74(6H, s), 2.98–3.04(4H, m), 3.29–3.52(2H, m), 5.26(2H, s), 5.35(1H, d, J=11Hz), 5.42(1H, d, J=11Hz), 5.80–5.90(1H, m), 6.30(1H, s), 6.87(1H, dq, J=7, 16Hz), 7.38–7.48(3H, m), 8.20(1H, d, J=3Hz), 9.46–9.63(1H, br), 10.35(1H, s).

$C_{35}$ mp 102–105° C., Yellow prisms (from n-Hexane-chloroform)
C$_{37}$H$_{43}$N$_4$O$_8$F, MS [M + H]$^+$ = 691,
IRν$^{MAX}$/$_{KBr}$ (cm$^{-1}$): 1710, 1650, 1620, 1600, 1505.
$^1$H-NMR (δppm) in CDCl$_3$: 1.14(3H, t, J=7Hz), 1.27(3H, t, J=8Hz), 2.16(6H, s), 2.22–2.42(3H, m), 2.49–2.62(1H, m), 2.82–3.18(3H, m), 3.18–3.42(1H, m), 3.39(3H, s), 3.50–3.64(2H, m), 3.80–3.93(2H, m), 4.94(1H, d, J=19Hz), 5.08(1H, d, J=19Hz), 5.35(1H, d, J=7Hz), 5.40(1H, d, J=7Hz), 5.55–5.77(1H, br), 5.78(2H, s), 7.01(2H, dd, J=9, 9Hz), 7.22(1H, d, J=3Hz), 7.27(1H, s), 7.35(1H, dd, J=3, 9Hz), 7.48(1H, br-t, J=6Hz), 7.50(1H, s), 7.90(1H, d, J=9Hz), 8.02(2H, dd, J=6, 9Hz).

$C_{36}$ mp 231–232° C., Colorless powder (from n-Hexane-chloroform)
$[α]^{25}/_D$ = −6.5(CH$_3$OH, c = 0.2), C$_{33}$H$_{35}$N$_4$O$_6$F, MS [M + H]$^+$ = 603,
IRν$^{MAX}$/$_{KBr}$ (cm$^{-1}$): 1710, 1645, 1620, 1585, 1520.
$^1$H-NMR (δppm) in DMSO-d$_6$: 0.91(3H, t, J=7Hz), 1.30(3H, t, J=8Hz), 2.11–2.30(2H, m), 2.53(6H, s), 2.62–2.90(2H, m), 2.99–3.40(4H, m), 5.29(2H, s), 5.57(1H, d, J=11Hz), 5.62(1H, d, J=11Hz), 6.36(1H, s), 7.33(1H, dd, J=9, 9Hz), 7.38–7.48(3H, m), 7.97(2H, dd, J=6, 9Hz), 8.04(1H, d, J=9Hz), 8.94–10.27(1H, br), 10.34(1H, s).

$C_{37}$ mp 105–109° C., Yellow prisms (from n-Hexane-chloroform)
$[α]^{25}/_D$ = +62.0(CHCl$_3$, c = 0.2), C$_{37}$H$_{43}$N$_4$O$_8$F, MS [M + H]$^+$ = 691,
Anal. (C, H, N): Found (calcd.) 63.02, 7.02, 8.67 (63.24, 7.02, 8.68),
IRν$^{MAX}$/$_{KBr}$ (cm$^{-1}$): 1710, 1620, 1585, 1510.
$^1$H-NMR (δppm) in CDCl$_3$: 1.14(3H, t, J=7Hz), 1.27(3H, t, J=8Hz), 2.16(6H, s), 2.23–2.43(3H, m), 2.50–2.66(1H, m), 2.83–3.05(1H, m), 3.06–3.19(1H, m), 3.27–3.44(1H, m), 3.39(3H, s), 3.50–3.63(2H, m), 3.80–3.92(2H, m), 4.95(1H, d, 19Hz), 5.08(1H, d, J=19Hz), 5.35(1H, d, J=7Hz), 5.40(1H, d, J=7Hz), 5.50–5.82(1H, br), 5.77(1H, d, J=12Hz), 5.81(1H, d, J=12Hz), 7.13–7.25(2H, m), 7.27–7.39 (2H, m), 7.48(1H, br-t, J=6Hz), 7.50(1H, s), 7.66–7.73(1H, m), 7.80(1H, d, J= 8Hz), 7.90(1H, d, J=9Hz).

$C_{38}$ mp 223–224° C., Colorless powder (from n-Hexane-chloroform)
C$_{33}$H$_{35}$N$_4$O$_6$F, MS [M + H]$^+$ = 603,

TABLE 3-continued (Spectral Data of 17-O-Acyl-21-amide Compounds)

IR$v^{MAX}/_{KBr}$ (cm$^{-1}$): 1710, 1645, 1620, 1590, 1520.
$^1$H-NMR (δppm) in DMSO-d$_6$: 0.91(3H, t, J=7Hz), 1.30(3H, t, J=8Hz), 2.08–2.34(2H, m), 2.54(6H, s), 2.54–2.75(2H, m), 2.95–3.43(4H, m), 5.29(2H, s), 5.58(1H, d, J=11Hz), 5.65(1H, d, J=11Hz), 6.35(1H, s), 7.34–7.68(6H, m), 7.76(1H, d, J=7Hz), 8.05(1H, d, J=9Hz), 8.08–8.22(1H, br), 9.22–9,66(1H, br), 10.32(1H, s)

C$_{39}$ mp 162–164° C., Yellow powder (from n-Hexane-chloroform)
C$_{33}$H$_{37}$N$_5$O$_5$.H$_2$O, MS [M + H]$^+$ = 584,
Anal. (C, H, N): Found (calcd.) 65.44, 6.53, 11.54 (65.87, 6.53, 11.64),
IR$v^{MAX}/_{KBr}$ (cm$^{-1}$): 1720, 1645, 1595, 1515
$^1$H-NMR (δppm) in CDCl$_3$: 1.13(3H, t, J=7Hz), 1.31(3H, t, J=8Hz), 2.16(6H, s), 2.27–2.42(3H, m), 2.51(3H, s), 2.52–2.63(1H, m), 2.90–3.14(3H, m), 3.30–3.41(1H, m), 4.89(1H, d, 19Hz), 5.10(1H, d, J=19Hz), 5.62–5.84(1H, br), 5.81(1H, d, J=12Hz), 5.86(1H, d, J=12Hz), 7.44–7.53(3H, m), 7.55(1H, s), 7.81(2H, dd, J=1, 5Hz), 7.89(1H, d, J=9Hz), 8.67(2H, dd, J=1, 5Hz).

C$_{40}$ mp 165–167° C., Yellow powder (from n-Hexane-chloroform)
C$_{32}$H$_{34}$N$_5$O$_5$Cl.½H$_2$O, MS [M + H]$^+$ = 604,
Anal. (C, H, N): Found (calcd.) 62.54, 5.78, 11.35 (62.69, 5.75, 11.42),
IR$v^{MAX}/_{KBr}$ (cm$^{-1}$): 1720, 1650, 1595, 1515
$^1$H-NMR (δppm) in CDCl$_3$: 1.14(3H, t, J=7Hz), 1.34(3H, t, J=8Hz), 2.16(6H, s), 2.27–2.41(3H, m), 2.52–2.64(1H, m), 2.93–3.13(3H, m), 3.30–3.30(1H, m), 5.01(1H, d, J=19Hz), 5.12(1H, d, J=19Hz), 5.51–5.57(1H, br), 5.80(1H, d, J=12Hz), 5.86(1H, d, J=12Hz), 7.49(1H, t, J=5Hz), 7.53(1H, s), 7.62(1H, dd, J=2, 9Hz), 7.70(1H, d, J=2Hz), 7.81(2H, dd, J=1, 5Hz), 7.90(1H, d, J=9Hz), 8.68(2H, dd, J=1, 5Hz).

C$_{41}$ mp ~171° C., Pale yellow powder (from n-Hexane-chloroform)
C$_{30}$H$_{34}$N$_4$O$_4$F, MS [M + H]$^+$ = 588,
IR$v^{MAX}/_{KBr}$ (cm$^{-1}$): 1720, 1650, 1595, 1510.
$^1$H-NMR (δppm) in CDCl$_3$: 1.15(3H, t, J=7Hz), 1.35(3H, t, J=8Hz), 2.16(6H, s), 2.27–2.42(3H, m), 2.52–2.66(1H, m), 2.98–3.18(3H, m), 3.29–3.40(1H, m), 5.02(1H, d, 19Hz), 5.12(1H, d, J=19Hz), 5.72–5.91(1H, br, D$_2$Oex.), 5.81(1H, d, J=12Hz), 5.87(1H, d, J=12Hz), 7.23(1H, ddd, J=3, 8, 10Hz), 7.52(1H, t, J=5Hz, D$_2$Oex.), 7.55(1H, s), 7.57(1H, dd, J=3, 10Hz), 7.80(2H, dd, J=2, 4Hz), 7.82(1H, dd, J=6, 9Hz), 8.67(2H, dd, J=2, 4Hz)

C$_{42}$ mp ~169° C., Pale yellow powder (from n-Hexane-chloroform)
C$_{31}$H$_{36}$N$_4$O$_4$F, MS [M + H]$^+$ = 602,
IR$v^{MAX}/_{KBr}$ (cm$^{-1}$): 1720, 1650, 1600, 1505.
$^1$H-NMR (δppm) in CDCl$_3$: 1.13(3H, t, J=7Hz), 1.36(3H, t, J=8Hz), 2.17(6H, s), 2.28–2.60(4H, m), 2.47(3H, m), 2.98–3.17(3H, m), 3.29–3.40(1H, m), 5.02(1H, d, J=19Hz), 5.13(1H, d, J=19Hz), 5.30–5.50(1H, br), 5.81(1H, d, J=12Hz), 5.84(1H, d, J=12Hz), 7.39(1H, br-t, J=5Hz, D$_2$Oex.), 7.52(1H, s), 7.54(1H, d, J=12Hz), 7.64(1H, d, J=8Hz), 7.81(2H, dd, J=2, 5Hz), 8.68(2H, dd, J=2, 5Hz).

C$_{43}$ mp 159–164° C., Yellow needles (from n-Hexane-chloroform)
C$_{31}$H$_{36}$N$_4$O$_5$F, MS [M + H]$^+$ = 618,
IR$v^{MAX}/_{KBr}$ (cm$^{-1}$): 1720, 1650, 1595, 1510.
$^1$H-NMR (δppm) in CDCl$_3$: 1.17(3H, t, J=7Hz), 1.30(3H, t, J=8Hz), 2.17(6H, s), 2.26–2.42(3H, m), 2.54–2.68(1H, m), 2.87–3.08(3H, m), 3.28–3.41(1H, m), 4.00(3H, s), 4.90(1H, d, J=19Hz), 5.04(1H, d, J=19Hz), 5.48–5.82(1H, br, D$_2$Oex.), 5.76(1H, d, J=12Hz), 5.86(1H, d, J=12Hz), 6.85(1H, d, J=9Hz), 7.45(1H, s,), 7.52(1H, t, J=6Hz, D$_2$Oex.), 7.55(1H, d, J=12Hz), 7.81(2H, dd, J=2, 5Hz), 8.67(2H, dd, J=2, 5Hz).

C$_{44}$ mp 147–150° C., Yellow powder (from n-Hexane-chloroform)
C$_{31}$H$_{33}$N$_5$O$_6$.H$_2$O, MS [M + H]$^+$ = 572,
Anal. (C, H, N): Found (calcd.) 62.85, 6.03, 11.78 (63.15, 5.98, 11.88),
IR$v^{MAX}/_{KBr}$ (cm$^{-1}$): 3390, 1710, 1650, 1615, 1590, 1520
$^1$H-NMR (δppm) in CDCl$_3$: 1.08(3H, t, J=7Hz), 2.15(6H, s), 2.29–2.55(4H, m), 3.22–3.41(2H, m), 4.02(3H, s), 5.14(1H, d, J=19Hz), 5.20(1H, d, J=19Hz), 5.34 (1H, br-s), 5.77(1H, d, J=12Hz), 5.94(1H, d, J=12Hz), 6.87(1H, d, J=8Hz), 7.39–7.47(2H, m), 7.60–7.68(2H, m), 7.73(1H, d, J=9Hz), 7.80(1H, ddd, J=2, 8, 8Hz), 8.13(1H, d, J=8Hz), 8.65–8.70(2H, m).

C$_{45}$

Colorless powder (from n-Hexane-chloroform)
C$_{28}$H$_{34}$N$_4$O$_6$, MS [M + H]$^+$ = 523,

TABLE 3-continued (Spectral Data of 17-O-Acyl-21-amide Compounds)

$C_{46}$

Yellow powder (from n-Hexane-chloroform)
$C_{30}H_{38}N_4O_6$, MS $[M + H]^+ = 551$, $C_{47}$ Yellow powder (from n-Hexane-chloroform)
$C_{31}H_{40}N_4O_7$, MS $[M + H]^+ = 581$, $C_{48}$ mp 179–182° C., Colorless powder (from n-Hexane-chloroform)
$C_{35}H_{37}N_4O_7F$, MS $[M + H]^+ = 645$,

TABLE 4

(Water solubility)

| Compd. No. | solubility (mg/ml) | Compd. No. | solubility (mg/ml) |
|---|---|---|---|
| $C_1$ | >64 | $C_{21}$ | >63 |
| $C_2$ | >67 | $C_{22}$ | >65 |
| $C_3$ | 29 | $C_{23}$ | 20 |
| $C_4$ | 41 | $C_{24}$ | 42 |
| $C_5$ | 21 | $C_{25}$ | >63 |
| $C_6$ | 25 | $C_{26}$ | 9 |
| $C_7$ | 21 | $C_{28}$ | >56 |
| $C_8$ | 20 | $C_{30}$ | >58 |
| $C_9$ | >59 | $C_{32}$ | >62 |
| $C_{10}$ | >62 | $C_{34}$ | >59 |
| $C_{11}$ | 8 | $C_{36}$ | 17 |
| $C_{12}$ | >64 | $C_{38}$ | 6 |
| $C_{13}$ | >59 | | |
| $C_{14}$ | >60 | | |
| $C_{15}$ | >64 | | |
| $C_{16}$ | 6 | | |
| $C_{17}$ | >64 | | |
| $C_{18}$ | 35 | | |
| $C_{19}$ | 24 | | |
| $C_{20}$ | >60 | | |

TABLE 5

(Antitumor activity of camptothecin derivatives)

| Compound No. | Optimum dose and antitumor activity | | | Therapeutic Index |
|---|---|---|---|---|
| | Total dose (mg/kg) | T/C % | 40-day survivors | (Maximum torelable dose/ Minimum effective dose) |
| $C_1$ | 6.25 | 252 | 0/6 | 4 (6.25/1.56) |
| $C_2$ | 25 | 214 | 0/6 | 8 (25/3.13) |
| $C_3$ | 6.25 | 275 | 1/6 | >4 (6.25/<1.56) |
| $C_4$ | 6.25 | 280 | 1/6 | >4 (6.25/<1.56) |
| $C_5$ | 6.25 | 295 | 3/6 | >4 (6.25/<1.56) |
| $C_6$ | 6.25 | 183 | 1/6 | >4 (6.25/<1.56) |
| $C_7$ | 100 | 368 | 5/6 | 32 (100/3.13) |
| $C_8$ | 12.5 | 364 | 4/6 | 8 (12.5/1.56) |
| $C_9$ | 12.5 | 293 | 2/6 | 8 (12.5/1.56) |
| $C_{10}$ | 12.5 | 240 | 1/6 | 8 (12.5/1.56) |
| $C_{11}$ | 50 | 243 | 0/6 | 8 (50/6.25) |
| $C_{12}$ | 25 | 281 | 1/6 | 16 (25/6.25) |
| $C_{13}$ | 1.56 | 214 | 0/6 | — |
| $C_{14}$ | 1.56 | 257 | 1/6 | — |
| $C_{15}$ | 1.56 | 260 | 0/6 | — |
| $C_{16}$ | 12.5 | 259 | 0/6 | 2 (12.5/6.25) |
| $C_{17}$ | 6.25 | 286 | 2/6 | 4 (6.25/1.56) |
| $C_{18}$ | 3.13 | 225 | 0/6 | >2 (3.13/<1.56) |
| $C_{19}$ | 3.13 | 198 | 0/6 | >2 (3.13/<1.56) |
| $C_{20}$ | 3.13 | 312 | 0/6 | >2 (3.13/<1.56) |
| $C_{21}$ | 3.13 | 265 | 0/6 | >2 (3.13/<1.56) |
| $C_{22}$ | 1.56 | 228 | 0/6 | — |
| $C_{23}$ | 12.5 | 317 | 0/6 | >8 (12.5/<1.56) |
| $C_{24}$ | 25 | 326 | 1/6 | >16 (25/1.56) |
| $C_{25}$ | 12.5 | 300 | 1/6 | >8 (12.5/<1.56) |
| $C_{26}$ | 50 | 264 | 0/6 | >4 (50/12.5) |
| $C_{28}$ | 200 | 180 | 0/6 | 16 (200/12.5) |
| $C_{30}$ | 200 | 235 | 0/6 | 32 (200/6.25) |
| $C_{32}$ | 200 | 198 | 0/6 | 32 (200/6.25) |
| $C_{36}$ | 200 | 214 | 0/6 | 16 (200/12.5) |
| $C_{38}$ | 200 | 226 | 0/6 | 16 (200/12.5) |
| $C_{39}$ | 50 | 376 | 3/6 | 16 (50/3.13) |
| $C_{40}$ | 12.5 | 266 | 1/6 | 4 (6.25/1.56) |
| $C_{41}$ | 25 | 300 | 2/6 | >16 (25/<1.56) |
| $C_{42}$ | 12.5 | 257 | 2/6 | >8 (12.5/1.56) |
| $C_{43}$ | 6.25 | 275 | 2/6 | >4 (6.25/1.56) |
| $C_{45}$ | 400 | 147 | 0/6 | 4 (400/100) |
| $C_{46}$ | 400 | 189 | 0/6 | 16 (400/25) |
| $C_{47}$ | 400 | 156 | 0/6 | 4 (200/50) |
| $C_{48}$ | 200 | 188 | 0/6 | 8 (200/25) |
| control CPT-Na salt | 60 | 203 | 0/6 | 6 (60/10) |

TABLE 6

(Acute Toxicity of camptotecin derivatives)

| Compd. No. | LD$_{50}$ value (mg/kg) | Compd. No. | LD$_{50}$ value (mg/kg) |
|---|---|---|---|
| $C_1$ | 164.5 | $C_{22}$ | 68.6 |
| $C_2$ | 241.1 | $C_{23}$ | 184.2 |
| $C_3$ | 185.6 | $C_{24}$ | 203.2 |
| $C_4$ | 142.4 | $C_{25}$ | 154.3 |
| $C_5$ | 167.5 | $C_{26}$ | 113.0 |
| $C_6$ | 116.3 | $C_{28}$ | 340.6 |
| $C_7$ | 234.5 | $C_{30}$ | 361.5 |
| $C_8$ | 124.5 | $C_{32}$ | 307.0 |
| $C_9$ | 152.1 | $C_{36}$ | 477.2 |
| $C_{10}$ | 145.8 | $C_{38}$ | 420.6 |
| $C_{11}$ | 146.1 | $C_{39}$ | 320.1 |
| $C_{12}$ | 284.5 | $C_{40}$ | 213.4 |
| $C_{13}$ | 67.6 | $C_{41}$ | 220.1 |
| $C_{14}$ | 98.3 | $C_{42}$ | 310.5 |
| $C_{15}$ | 85.2 | $C_{43}$ | 164.9 |
| $C_{16}$ | 65.6 | $C_{45}$ | 376.2 |
| $C_{17}$ | 112.0 | $C_{46}$ | 478.3 |
| $C_{18}$ | 92.3 | $C_{47}$ | 471.2 |
| $C_{19}$ | 94.8 | $C_{48}$ | 418.3 |
| $C_{20}$ | 84.5 | Control CPT-Na salt | 227.0 |
| $C_{21}$ | 124.3 | | |

What is claimed is:

1. A camptothecin compound of the formula (1)

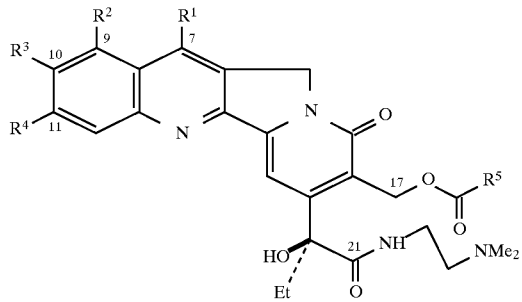

wherein $R^1$ represents a hydrogen atom or a $C_1$–$C_6$ alkyl group, $R^2$ represents a hydrogen or a $C_1$–$C_6$ alkoxy group, $R^3$ represents a hydrogen or halogen atom or a $C_1$–$C_6$ alkyl, $C_1$–$C_6$ alkoxy, hydroxyl, $C_2$–$C_6$ acyloxy or methoxyethoxymethoxy group, $R^4$ represents a hydrogen or halogen atom, and $R^5$ represents a $C_1$–$C_6$ alkyl, $C_3$–$C_6$ unsaturated alkyl, lower alkylthio lower alkyl, lower alkoxy lower alkyl, pyridyl or a mono- or di substituted phenyl group, with the proviso that all of the $R^2$, $R^3$ and $R^4$ substituents should not be a hydrogen atom.

2. An antitumor agent containing as an active ingredient a camptothecin compound of the formula (1) according to claim 1.

* * * * *